United States Patent
Venter et al.

(10) Patent No.: US 9,399,179 B2
(45) Date of Patent: Jul. 26, 2016

(54) SEPARATION OF COMPONENTS FROM A MULTI-COMPONENT HYDROCARBON STREAM

(71) Applicant: SASOL TECHNOLOGY (PROPRIETARY) LIMITED, Johannesburg (ZA)

(72) Inventors: Denise Louisette Venter, Vaalpark (ZA); Natasha Brigman, Vanderbijlpark (ZA); Tyrone McKnight, Vanderbijlpark (ZA); Kevin Blann, Alberton (ZA); Stephen John Evans, Roodepoort (ZA)

(73) Assignee: SASOL TECHNOLOGY PROPRIETARY LIMITED, Johannesburg (ZA)

( * ) Notice: Subject to any disclaimer, the term of this patent is extended or adjusted under 35 U.S.C. 154(b) by 95 days.

(21) Appl. No.: 14/396,471

(22) PCT Filed: May 8, 2013

(86) PCT No.: PCT/IB2013/053686
§ 371 (c)(1),
(2) Date: Oct. 23, 2014

(87) PCT Pub. No.: WO2013/168098
PCT Pub. Date: Nov. 14, 2013

(65) Prior Publication Data
US 2015/0133707 A1    May 14, 2015

(30) Foreign Application Priority Data

May 9, 2012    (ZA) .................................. 2012/03386

(51) Int. Cl.
| | | |
|---|---|---|
| C08F 2/00 | (2006.01) | |
| C08F 210/00 | (2006.01) | |
| C07C 2/24 | (2006.01) | |
| B01D 3/10 | (2006.01) | |
| B01D 3/06 | (2006.01) | |
| C07C 2/36 | (2006.01) | |
| B01D 3/00 | (2006.01) | |
| B01D 3/14 | (2006.01) | |

(52) U.S. Cl.
CPC ........ B01D 3/06 (2013.01); B01D 3/009 (2013.01); B01D 3/148 (2013.01); C07C 2/36 (2013.01); *B01D 3/143* (2013.01); *C07C 2531/14* (2013.01); *C07C 2531/24* (2013.01)

(58) Field of Classification Search
CPC ........ C07C 2/36; C07C 11/107; C07C 11/02; C07C 2531/14; C07C 2531/24; B01D 3/009; B01D 3/148; B01D 3/06; B01D 3/143
USPC ................... 585/514; 203/80, 88; 526/64, 348
See application file for complete search history.

(56) References Cited

U.S. PATENT DOCUMENTS

| | | |
|---|---|---|
| 4,229,607 A | 10/1980 | Gum et al. |
| 4,668,838 A | 5/1987 | Briggs |
| 5,750,817 A | 5/1998 | Tanaka |
| 5,811,618 A | 9/1998 | Wu |
| 6,031,145 A | 2/2000 | Commereuc |
| 2006/0247399 A1 | 11/2006 | McConville et al. |
| 2008/0027188 A1 | 1/2008 | Small et al. |
| 2008/0242811 A1 | 10/2008 | Gao et al. |

FOREIGN PATENT DOCUMENTS

| | | |
|---|---|---|
| EP | 0668105 | 9/2002 |
| EP | 2 488 473 B1 * | 12/2013 |
| WO | WO 03/053890 | 7/2003 |
| WO | WO 2004/056477 | 7/2004 |
| WO | WO 2004/056478 | 7/2004 |
| WO | WO 2004/056479 | 7/2004 |
| WO | WO 2004/056480 | 7/2004 |
| WO | WO 2005/123633 | 12/2005 |
| WO | WO 2005/123884 | 12/2005 |
| WO | WO 2006/108803 | 10/2006 |
| WO | WO 2007/007272 | 1/2007 |
| WO | WO 2007/039851 | 4/2007 |
| WO | WO 2007/057455 | 5/2007 |
| WO | WO 2007/088329 | 8/2007 |
| WO | WO 2008/038173 | 4/2008 |

| WO | WO 2008/077908 | 7/2008 |
| WO | WO 2008/077911 | 7/2008 |
| WO | WO 2008/088178 | 7/2008 |
| WO | WO 2009/006979 | 1/2009 |
| WO | WO 2009/022770 | 2/2009 |
| WO | WO 2010/092554 | 8/2010 |
| WO | WO 2011/048527 | 4/2011 |

OTHER PUBLICATIONS

Arteaga-Muller, R, Tsurugi, H., Saito, T. Yanagawa, M, Oda, S. and Mashima, K., J.A.C.S Communications, 2009, 131 5370-5371.

D.E. Bergbreiter et al., J. Am. Chem. Soc., 1987, 109, 177-179.

International Preliminary Report on Patentability issued for International PCT Application No. PCT/IB2013/053686.

* cited by examiner

*Primary Examiner* — William Cheung

(74) *Attorney, Agent, or Firm* — K&L Gates LLP

(57) ABSTRACT

A process (10) to separate a multi-component hydrocarbon stream (26) comprising ethylene, at least one polymer and other components includes flashing the multi-component hydrocarbon stream in a first flash stage (12) from an elevated pressure of more than 30 bar(a) and an elevated temperature in the range of 150° C. to 135° C. to a flash pressure in the range of 10 bar(a) to 30 bar(a), producing a first ethylene-containing vapor overheads product (28) at a pressure in the range of 10 bar(a) to 30 bar(a) and a first flash stage bottoms product (30.1) which includes some ethylene, the at least one polymer and some of the other components. The flash pressure and the elevated temperature of the multi-component hydrocarbon stream (26) are selected such that the first flash stage bottoms product (30.1) has a concentration of the at least one polymer of less than 5% by mass to render the viscosity of the first flash stage bottoms product (30.1) at the temperature of the first flash stage bottoms product (30.1) in the first flash stage (12) at less than 1000 cP at a shear of 1 per second. At least a portion of the first flash stage bottoms product (30.1) is heated to a temperature in excess of 150° C. to form a heated first flash stage bottoms product (30.2). A recycle portion (30.3) of the heated first flash stage bottoms product (30.2) is combined with the multi-component hydrocarbon stream (26), which is at a temperature less than 150° C. before combination with the recycle portion (30.3), thereby to heat the multi-component hydrocarbon stream (26) to the elevated temperature in the range of 150° C. to 185° C. At least a portion (32) of the first flash stage bottoms product and the first ethylene-containing vapor overheads product (28) are withdrawn from the first flash stage (12).

14 Claims, 3 Drawing Sheets

US 9,399,179 B2

SEPARATION OF COMPONENTS FROM A MULTI-COMPONENT HYDROCARBON STREAM

PRIORITY CLAIM AND CROSS-REFERENCE TO RELATED APPLICATIONS

Figure 1:
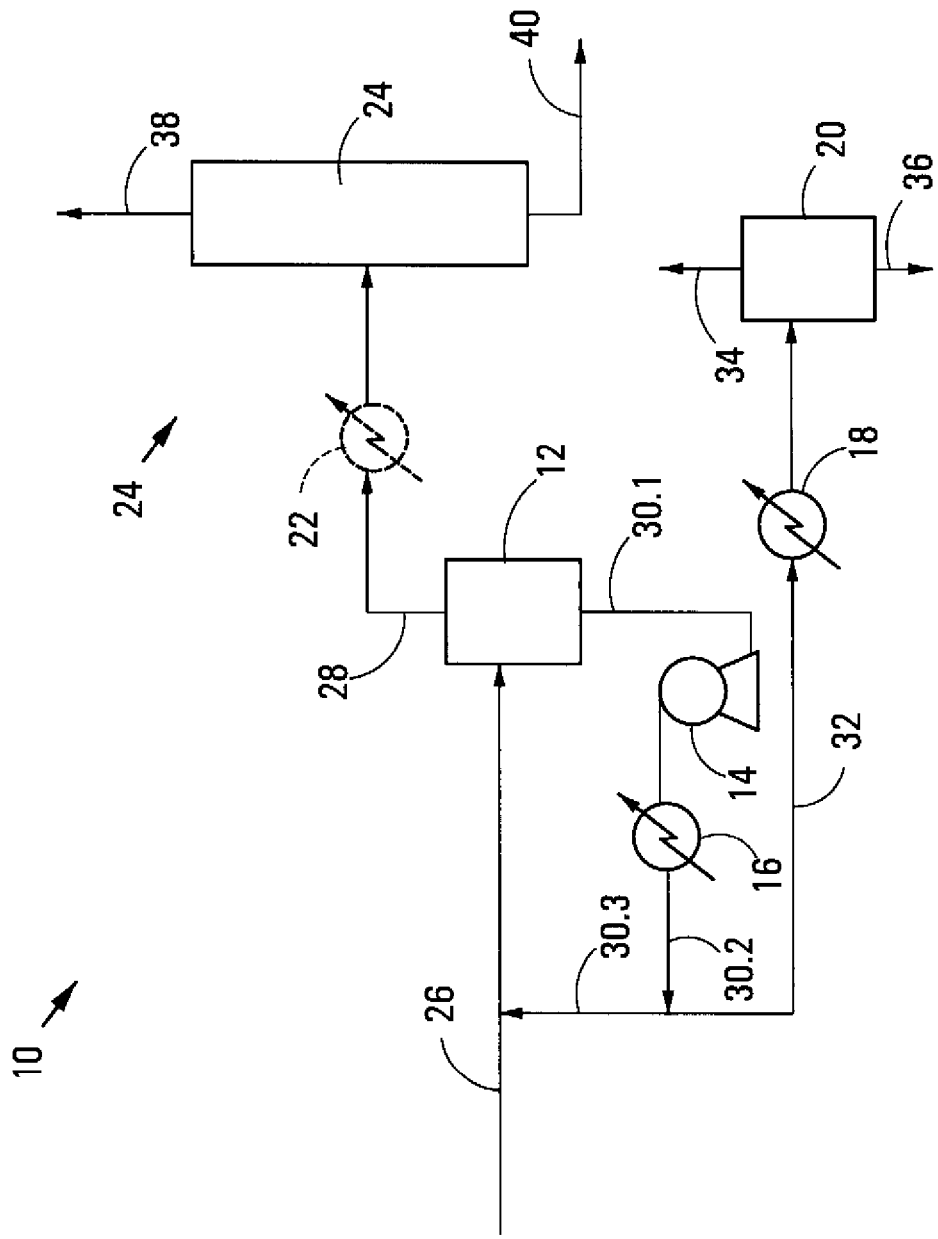

This application claims the benefit under 35 U.S.C. §371 to International Application Number PCT/IB2013/053686, filed on 8 May 2013, which claims the priority of South African Application Number 2012/03386, filed on 9 May 2012, to which priority is also claimed by the present application. The entire disclosure of both of said applications is incorporated by reference herein.

THIS INVENTION relates to separation of components from a multi-component hydrocarbon stream which includes ethylene and at least one polymer. In particular, the invention relates to a process to separate a multi-component hydrocarbon stream which includes ethylene, at least one polymer and other components, and to an ethylene oligomerisation process which includes this separation process.

Distillation is the method of choice for many processes to separate a multi-component hydrocarbon stream into different fractions. When the multi-component hydrocarbon stream includes solids, whether molten, dissolved or not dissolved, such as polymers and waxes, it is undesirable to feed the multi-component hydrocarbon stream over distillation trays, as the solids may block the trays. One example of such a multi-component hydrocarbon stream is the oligomeric product stream obtained from the oligomerisation of an olefinic feedstock. Thus, processes for polymerising or oligomerising a hydrocarbon to form an alpha monomer or co-monomer are complicated by the fact that polymeric by-product is formed which coats process equipment surfaces, precluding the use of conventional heat transfer equipment such as shell and tube heat exchangers, and precluding the use of conventional solid-liquid separators for removing the polymeric by-product from the liquid product slate typically including alpha monomer or co-monomer polymeric or oligomeric product, unreacted hydrocarbon reactant and diluent solvent.

Instead of implementing distillation or a solid-liquid separation process such as filtration, the oligomeric product stream can be flashed to separate more volatile components of the product stream from less volatile components of the product stream. Flashing however has a number of potential complications. For example, there is the potential to foul any heat exchange equipment used to heat the oligomeric product stream prior to flashing in a flash stage to ensure that any polymer is molten and in solution. In addition, a highly viscous non-Newtonian polymer solution may be formed as a bottoms stream from the flash stage as a result of the concentration of the polymer in the bottoms stream. For such high viscosity, non-Newtonian solutions with low heat transfer coefficients, specialised pumps and heat exchange equipment are required. Such specialised pumps and heat exchange equipment are expensive and therefore undesirable. Flashing also has the potential to lead to high ethylene losses to the bottoms stream.

A reaction solvent or diluent solvent, i.e. an inert liquid component which does not take part in a polymerisation or oligomerisation reaction and which is not required to ensure that the polymerisation or oligomerisation reaction takes place, is often used in a process for the polymerising or oligomerising, e.g. tetramerisation, of a hydrocarbon such as ethylene, to reduce secondary incorporation of alpha monomer or co-monomer products, e.g. 1-hexene or 1-octene, into undesirable longer chain products of less value, by diluting the concentration of the primary reaction product or products. This diluent solvent may be distinguished from a catalyst solvent which is typically required to dissolve components of a catalyst system required for the polymerising or oligomerising process, although it is possible that the same solvent may be used as a catalyst solvent and as a diluent solvent. Recovery of the diluent solvent for recycle is energy intensive and any ethylene oligomerisation process must thus be designed with this in mind.

A catalyst solvent in a process for polymerising or oligomerising a hydrocarbon to form an alpha monomer or co-monomer is a liquid component in which one or more catalyst precursor components (e.g. active metal precursor, ligand or catalyst activator) are dissolved so as to facilitate catalyst transport from a catalyst feed supply into a bulk liquid phase in which the polymerisation or oligomerisation takes place.

An efficient and economical process to separate a multi-component hydrocarbon stream which includes ethylene and at least one polymer, which may be present as a solid, would thus be desirable.

According to one aspect of the invention, there is provided a process to separate a multi-component hydrocarbon stream which includes ethylene, at least one polymer and other components, the process including in a first flash stage, flashing the multi-component hydrocarbon stream, from an elevated pressure of more than 30 bar(a) and an elevated temperature in the range of 150° C. to 185° C. to a flash pressure in the range of 10 bar(a) to 30 bar(a), producing a first ethylene-containing vapour overheads product at a pressure in the range of 10 bar(a) to 30 bar(a) and a first flash stage bottoms product which includes some ethylene, said at least one polymer and some of said other components, the flash pressure and the elevated temperature of the multi-component hydrocarbon stream being selected such that the first flash stage bottoms product has a concentration of said at least one polymer of less than 5% by mass to render the viscosity of the first flash stage bottoms product at the temperature of the first flash stage bottoms product in the first flash stage at less than 1000 cP at a shear of 1 per second;

heating at least a portion of the first flash stage bottoms product to a temperature in excess of 150° C. to form a heated first flash stage bottoms product;

combining a recycle portion of said heated first flash stage bottoms product with the multi-component hydrocarbon stream, which is at a temperature less than 150° C. before combination with said recycle portion, thereby to heat the multi-component hydrocarbon stream to said elevated temperature in the range of 150° C. to 185° C.;

withdrawing at least a portion of the first flash stage bottoms product which includes some ethylene, said at least one polymer and some of said other components, from the first flash stage; and removing the first ethylene-containing vapour overheads product from the first flash stage.

The first flash stage may be the only flash stage used to separate said at least one polymer from ethylene and said some other components. Typically however, the process includes feeding at least a portion of the first flash stage bottoms product to a second flash stage as a second flash stage feed.

The process may include, in the second flash stage, flashing the second flash stage feed to produce a second vapour overheads product which includes most of the ethylene in the second flash stage feed, and a second flash stage bottoms product which includes most of said at least one polymer in the second flash stage feed.

The process typically includes removing the second vapour overheads product from the second flash stage and removing the second flash stage bottoms product from the second flash stage.

The process may include separating at least a portion of the ethylene from the first ethylene-containing vapour overheads product removed from the first flash stage. Thus, the first ethylene-containing vapour overheads product removed from the first flash stage may be subjected to at least one ethylene recovery unit operation producing an ethylene-rich stream and an ethylene-poor multi-component hydrocarbon stream.

The process may include the further step of condensing or partially condensing the second vapour overheads product from the second flash stage to produce a condensate and feeding the condensate to the ethylene recovery unit operation.

The multi-component hydrocarbon stream is thus heated by direct contact heating or mixing with a hot process stream, i.e. the recycle portion of the heated first flash stage bottoms product, producing a combined stream which is then flashed in the first flash stage. Any polymer present in the multi-component hydrocarbon stream, if present as a solid, melts and dissolves at said elevated temperature of more than 150° C. without a heat exchanger which could foul being required. The first flash stage bottoms product is however heated to a temperature below the lower critical solution temperature of the first stage bottoms product stream so that any liquid portion of said first stage bottoms product stream remains a single liquid phase and does not form any significant amount of a second polymer-rich liquid phase.

Said other components of the multi-component hydrocarbon stream may include oligomers or olefins, in particular one or more alpha monomers (e.g. 1-butene and/or ethylene) or co-monomers (e.g. 1-hexene and/or 1-octene), and/or a diluent solvent (e.g. iso-octane, cyclohexane, methylcyclohexane, propane, isobutane, isopentane, neopentane, 2-methylpentane, or 3-methylpentane), and/or a catalyst solvent, and/or a dissolved catalyst and/or a dissolved catalyst activator).

Typically, the at least one polymer in the multi-component hydrocarbon stream is a polymeric by-product, e.g. a polymeric by-product of the tetramerisation or trimerisation of ethylene to form an alpha monomer or co-monomer. In this specification, the term "polymer" is thus intended to distinguish polymeric by-product, which may be solid or molten at typical process conditions, from the desirable oligomeric product that may be present in the multi-component hydrocarbon stream and which is never solid at typical process conditions.

The concentration of polymers in the first flash stage bottoms product is preferably less than 3% by mass. Even more preferably, the concentration of polymers in the first flash stage bottoms product is less than 2.8% by mass.

In essence, by manipulating the temperature and the pressure of the first flash stage according to the process of the invention, the concentration of polymers in the first flash stage bottoms product is limited to a value which provides a solution viscosity of less than 1000 cP at a shear of 1 per second at the temperature of the first flash stage bottoms product. Operating conditions of the first flash stage required to attain the desired polymer concentration and therefore polymer solution viscosity in the first flash stage bottoms product will depend on the composition of the multi-component hydrocarbon stream, and in particular on any diluent solvent present in the multi-component hydrocarbon stream.

As may be appreciated the lower the polymer concentration in the first flash stage bottoms product the lower the solution viscosity of the first flash stage bottoms product.

Operating the first flash stage at conditions suitable to dilute the polymer concentration in the first flash stage bottoms product is counter intuitive as the conventional approach is that the conditions in such a first flash stage should be manipulated to recover as much monomer, i.e. ethylene, as possible in the first ethylene-containing vapour overheads product from the first flash stage, implying achieving as concentrated a polymer concentration as possible in the first flash stage bottoms product. To the best of the inventors' knowledge, it has never before been suggested that the polymer is to be diluted at the expense of losing valuable monomer in the first flash stage bottoms product.

Advantageously, by diluting the polymer concentration in the first flash stage bottoms product one can exploit the viscosity ranges that can be managed by certain less expensive types of heat exchangers and pumps. At solution viscosities above 1000 cP at a shear of 1 per second, comparatively inexpensive centrifugal pumps and conventional shell and tube heat exchangers cannot effectively be used. However, by limiting solution viscosities to below 1000 cP at a shear of 1 per second comparatively inexpensive centrifugal pumps and conventional shell and tube heat exchangers can be used and the capital and operating costs for the first flash stage can be substantially reduced making it viable to reduce recovery of expensive monomer to the first ethylene-containing vapour overheads product from the first flash stage.

The process may therefore include using one or more conventional centrifugal pumps to pump the first flash stage bottoms product from the first flash stage to form the second flash stage feed and in order to combine the recycle portion of the heated first flash stage bottoms product with the multi-component hydrocarbon stream. Typically, the discharge pressure of the centrifugal pump or pumps is sufficiently high substantially to prevent vapourisation of any part of the heated first flash stage bottoms product.

The portion of the first flash stage bottoms product, i.e. a non-recycle portion of the first flash stage bottoms product, fed to the second flash stage as the second flash stage feed may be split off from the heated first flash stage bottoms product. Typically, the entire first flash stage bottoms product is withdrawn from the first flash stage and heated, before being split into the recycle portion of the heated first flash stage bottoms product and the second flash stage feed.

Typically the second flash stage feed is heated further before being fed to the second flash stage, i.e. before flashing the second flash stage feed in the second flash stage. Typically, the discharge pressure of said one or more centrifugal pumps is sufficiently high substantially to prevent vaporisation of any part of the heated second flash stage feed before it undergoes flashing in the second flash stage. Alternatively, the portion of the heated first flash stage bottoms product which forms the second flash stage feed may be pumped up further with at least one second centrifugal pump to a pressure sufficiently high to substantially prevent vaporisation of any part of the heated second flash stage feed before it undergoes flashing in the second flash stage.

The process may include feeding the second flash stage bottoms product, i.e. a polymer-rich liquid product, to a devolatiliser to produce a polymeric solids product. Typically, the devolatiliser also produces a vapour stream, which may be flared, processed further or joined with another process stream for further treatment or processing. The polymeric solids product may be subjected to a solids work-up operation, which may for example employ an underwater pelletiser to pelletise the polymeric solids.

According to a second aspect of the invention, there is provided an ethylene oligomerisation process, the process including in an oligomerisation stage, oligomerising ethylene and withdrawing a multi-component hydrocarbon stream which includes unreacted ethylene, at least one polymer and other components;

separating the multi-component hydrocarbon stream in accordance with a process as hereinbefore described, producing said first ethylene-containing vapour overheads product and said second vapour overheads product;

feeding the first ethylene-containing vapour overheads product to an ethylene recovery unit operation producing an ethylene-rich stream and an ethylene-poor multi-component hydrocarbon stream which includes oligomeric product;

recycling the ethylene rich stream to the oligomerisation stage;

recovering ethylene from the second vapour overheads product; and recycling said ethylene recovered from the second vapour overheads product to the oligomerisation stage.

The ethylene-poor multi-component hydrocarbon stream may include a solvent for an ethylene oligomerisation catalyst.

The ethylene-poor multi-component hydrocarbon stream may include a diluent solvent.

In conventional processes of which the inventors are aware, due to the fact that the pressure and temperature of the first flash stage are manipulated to recover as much ethylene as possible to the first ethylene-containing vapour overheads product from the first flash stage, the amount of ethylene present in the second vapour overheads product from the second flash stage is minimal and it is therefore not economically viable to recover the ethylene for recycle to the oligomerisation reactor. As will be appreciated, as a result of the deliberate operation of the first flash stage to obtain a dilute polymer concentration, and hence a low viscosity in the first flash stage bottoms product, ethylene losses (and losses of other valuable components in the multi-component hydrocarbon stream, such as a diluent solvent) to the first flash stage bottoms product, and ultimately to the second flash stage, are increased. Recovering of ethylene from the second vapour overheads product for recycle to the oligomerisation stage is thus an important process step in the process according to the second aspect of the invention. The challenge inherent in this recovery step is that the ethylene must be recovered from a vapour stream which is at a pressure substantially lower than the pressure of the ethylene recovery unit operation and the oligomerisation stage.

In order to address this challenge, the process in accordance with the second aspect of the invention may include at least partially condensing the second vapour overheads product from the second flash stage to provide a second flash stage condensate product. As this second flash stage condensate product is a liquid it may advantageously easily be pumped up to the pressure of the ethylene recovery unit operation eliminating the need for a compressor which substantially reduces capital and operating costs. If any part of the second vapour overheads product is not condensed, the process may include separating the second flash stage condensate product and the uncondensed portion of the second vapour overheads product, providing a second flash stage uncondensed vapour product.

In one embodiment of the process according to the second aspect of the invention, said process thus includes at least partially condensing the second vapour overheads product from the second flash stage to provide a second flash stage condensate product; and pumping the second flash stage condensate product to said ethylene recovery unit operation, recovering ethylene from the second vapour overheads product thus being effected in said ethylene recovery unit operation.

Surprisingly, simulations show that the temperature/pressure combinations required to condense all of the ethylene present in the second vapour overheads product and therefore to substantially completely recover all ethylene and any diluent solvent that may be present are reasonable and comparatively insensitive to both the diluent solvent used as well as the polymer concentration and hence the viscosity or the degree of dilution/viscosity of the first flash stage bottoms product.

In one embodiment of the invention, plant cooling water, i.e. unrefrigerated plant cooling water, is used as cooling medium partially to condense the second vapour overheads product. This is important as cooling water is a much cheaper and more readily available utility than refrigerant or chilled cooling water. Surprisingly, simulations show that a significant portion of the ethylene in the second vapour overheads product can be recovered at pressures ranging between 4 bar(a) and 10 bar(a), using plant cooling water only.

The ethylene may be oligomerised in the presence of a diluent solvent, the diluent solvent being selected from the group consisting of iso-octane, iso-pentane, neopentane, isobutane and mixtures of two or more of these.

The diluent solvent present in the second vapour overheads product does have an effect on the ethylene recovery possible using plant cooling water only. From this perspective, iso-octane, iso-pentane, neopentane and isobutane are preferred, in this order.

The process may include recovering ethylene from the second stage uncondensed vapour product by absorbing the second stage uncondensed vapour product into a liquid process stream and employing the liquid process stream where ethylene is useful or desirable.

The process may include feeding the second flash stage condensate to the same ethylene recovery unit operation in which ethylene is recovered from the first ethylene-containing vapour overheads product and recovering ethylene and possibly diluent solvent (depending on the normal boiling point of the diluent solvent) from said second flash stage condensate in the ethylene recovery unit operation to form part of the ethylene-rich stream for recycle to the oligomerisation stage. Preferably, the second flash stage condensate being fed to the ethylene recovery unit operation is at a temperature no higher than that of the first ethylene-containing vapour overheads product being fed into the ethylene recovery unit operation so as not to place additional load on any condenser used in the ethylene recovery unit operation.

The second flash stage feed is preferably flashed in the second flash stage to a pressure of between about 1 bar(a) and about 6 bar(a), more preferably between about 2 bar(a) and about 5 bar(a), e.g. between about 2 bar(a) and about 4 bar(a). In some embodiments of the invention however, a negative gauge pressure, i.e. a subatmospheric pressure, may be used in the second flash stage.

Typically, the ethylene recovery unit operation employs at least one distillation column. The ethylene recovery unit operation, and in particular said distillation column, may be operated at the same pressure as the first flash stage, minus any pressure drop caused by intervening process equipment. The ethylene recovery unit operation, and in particular said distillation column, may thus operate at a pressure in the range of about 10-28 bar(a), preferably about 10-15 bar(a).

The first ethylene-containing vapour overheads product being fed to the ethylene recovery unit operation is typically not recompressed before being fed into the ethylene recovery unit operation, but is preferably at least partially condensed before being fed into the ethylene recovery unit operation.

Preferably, from a thermodynamic point of view, the second flash stage condensate being fed to the ethylene recovery unit operation, and in particular to said distillation column, is fed at a separate feed point on the distillation column than the first ethylene-containing vapour overheads product being fed to the distillation column. The preferred location of the second flash stage condensate feed point depends on the diluent solvent used in the ethylene oligomerisation process.

The ethylene-poor multi-component hydrocarbon stream from the ethylene recovery unit operation may include alpha monomers or co-monomers, e.g. 1-hexene, 1-octene and/or 1-butene. The multi-component hydrocarbon stream may also include cyclic by-products of ethylene oligomerisation, C10+ hydrocarbons, aliphatic or aromatic solvent, ethane, very small if any quantities of methane, and polymer(s). Most methane and ethane in fact reports to the ethylene rich stream from the ethylene recovery unit operation.

In the oligomerisation stage, the ethylene is preferably oligomerised at an elevated pressure of at least 30 bar(a) and at an elevated temperature, typically at least 40° C. The elevated pressure may be between about 30 bar(a) and about 50 bar(a), preferably between about 40 bar(a) and about 50 bar(a), more preferably between about 46 bar(a) and about 50 bar(a). The elevated temperature of the oligomerisation stage is typically between about 40° C. and about 80° C., e.g. about 60° C.

In one embodiment of the invention, the process in accordance with the second aspect of the invention is a broad range ethylene oligomerisation process, employing a catalyst system and yielding a Schulz Flory or Poisson distribution of olefins. The olefins from this process find application as feedstock for detergents, plasticiser alcohols, linear alkyl benzenes and as co-monomers for the production of polyethylene. Non-limiting examples of such catalyst systems are nickel based systems bearing α-diimine ligands and activated by a dialkyl aluminium halide cocatalyst (e.g. as described in WO 0010945), or nickel based systems having chelating ligands such as 2-diphenyl phosphine benzoic acid in combination with a borohydride reducing agent (e.g. as described in U.S. Pat. No. 3,676,523). Also possible is the use of trialkylaluminium catalysts for the production of a broad range of alpha olefins.

In a further embodiment of the invention, the process in accordance with the second aspect of the invention is predominantly a trimerisation of ethylene process. The trimerisation of ethylene to 1-hexene is a significant commercial operation. In addition to its use as a specific chemical, 1-hexene is extensively used in polymerisation processes either as a monomer or co-monomer. Non-limiting examples of ethylene trimerisation catalyst systems are provided in a review by Dixon, J. T., Green, M. J., Hess, F. M., and Morgan, D. H., Journal of Organometallic Chemistry, 2004, 689, 3641-3668. A few examples include the Phillips Cr/pyrollide/TEA system, the Dutch Polymer Institute Ti/benzyl substituted Cp/MAO system, the BP Cr/o-methoxyphenylPNP/MAO system and the Sasol Cr/SNS/MAO and Cr/o-alkylphenylPNP/MAO systems. Examples of ligand-free, tantalum-based catalyst systems have also been reported by Arteaga-Muller, R, Tsurugi, H., Saito, T, Yanagawa, M, Oda, S. and Mashima, K., J.A.C.S Communications, 2009, 131, 5370-5371.

In another embodiment of the invention, the process in accordance with the second aspect of the invention is predominantly a tetramerisation of ethylene process. As in the case of 1-hexene described above, 1-octene is also used as a co-monomer in the production of linear low density polyethylene. Non limiting examples of selective ethylene tetramerisation catalyst systems include the ubiquitous Cr/PNP/MAO systems, beginning with PNP ligands containing no substituents on the phenyl rings attached to the P-atoms (e.g. as described in WO 2004/056479) and those with p-methoxy groups on the phenyl rings (e.g. as described in WO 2004/056480). In addition to this, PNP systems containing o-fluoro groups on the phenyl rings are described in US2008/0242811, and PNP systems bearing pendant donor atoms on the nitrogen linker are described in WO2007/088329. Multi-site PNP ligands are discussed in US2008/0027188.

In addition to the Cr/PNP systems, chromium systems bearing N,N-bidentate ligands (e.g. as described in US 2006/0247399) as well as systems containing PPN ligands (e.g. as described in WO2008/077911 and WO2008/077908) can be used. PNPNH as well as PNPNP ligands are described in WO2009/006979. Finally, chromium/PCCP/MAO systems are described in WO2008/088178 and WO2009/022770.

In a further embodiment, the process in accordance with the second aspect of the invention is predominantly both a trimerisation process and a tetramerisation process. In yet a further embodiment, the process in accordance with the second aspect of the invention is a tetramerisation of ethylene process in combination with a trimerisation of ethylene process, or broad range oligomerisation of ethylene process, as described in WO 2005/123884. The process may be a combination of a tetramerisation of ethylene and trimerisation of ethylene process as described in WO 2005/123884, WO 2007/057455 and WO 2006/108803. The process may also be a tandem oligomerisation/polymerisation process as discussed in WO 2004/056480.

In one embodiment of the invention, the catalyst is a dissolved transition metal compound catalyst, e.g. a chromium catalyst, with a heteroatomic or homoatomic, ligand, typically used with an activator. A number of dissolved transition metal compound catalysts have been developed for use to trimerise or tetramerise olefins, e.g. as disclosed in U.S. Pat. No. 4,668,838; EP 0668105; U.S. Pat. No. 5,750,817; U.S. Pat. No. 6,031,145; U.S. Pat. No. 5,811,618; WO 03/053890; WO 2004/056478; WO 2004/056477; WO 2004/056479; WO 2004/056480; WO 2005/123633 and WO 2007/007272.

Some of these catalysts are selective for $C_6$ and $C_8$ oligomeric products, e.g. 1-hexene and 1-octene, and the Applicant believes that such catalysts will be particularly advantageous for use with the process according to the second aspect of the invention as the selective production of 1-hexene and 1-octene from ethylene is commercially important. In one embodiment of the invention, the catalyst is preferably a tetramerisation catalyst which produces at least 30% 1-octene.

In a preferred embodiment of the process in accordance with the second aspect of the invention the catalyst also includes one or more activators. Such an activator may be a compound that generates an active catalyst when the activator is combined with a source of transition metal and a ligating compound.

Suitable activators include organoaluminium compounds, boron compounds including those disclosed in WO2010/092554 and WO2011/048527, aluminate activators including those disclosed in WO 2008/038173 and WO2007/039851 e.g. trityl perfluoro-tributyl aluminate, and the like. Such activators may optionally be used in combination with alkylaluminium or alkylzinc compounds.

Suitable organoaluminium compounds include compounds of the formula $Al(R^1)_3$ ($R^1$ being the same or different), where each $R^1$ is independently a $C_1$-$C_{12}$ alkyl, an oxygen containing moiety or a halide, aluminoxanes, and compounds such as $LiAlH_4$ and the like. Aluminoxanes are well known in the art as typically oligomeric compounds which can be prepared by the controlled addition of water to an alkylaluminium compound, for example trimethylaluminium. In such process the alkylaluminium compounds are only partially hydrolysed to prevent or at least to reduce the formation of aluminium hydroxide during the preparation of aluminoxanes. Commercially available aluminoxanes consequently include unreacted alkylaluminium. The result is that commercially available aluminoxanes are usually mixtures of an aluminoxane and an alkylaluminium. Such compounds can be linear, cyclic, cages or mixtures thereof. Examples of suitable aluminium compounds in the form of organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, $[Ph_3C][Al\{OC(CF_3)_3\}]$, methylaluminoxane (MAO), ethylaluminoxane (EAO), isobutylaluminoxane (iBuAO), modified alkylaluminoxanes such as modified methylaluminoxane (MMAO) and mixtures of the above-mentioned compounds.

In this specification the term "aluminoxanes" is used to denote a compound represented by the general formulae $(R^a-Al-O)_n$ and $R^b(R^c-Al-O)_n-AlR^d_2$ wherein $R^a$, $R^b$, $R^c$, and $R^d$ are independently a $C_1$-$C_{30}$ alkyl or halo-alkyl radical, for example methyl, ethyl, propyl, butyl, 2-methyl-propyl, pentyl, isopentyl, neopentyl, cyclopentyl, hexyl, isohexyl, cyclohexyl, heptyl, octyl, iso-octyl, 2-ethyl-hexyl, decyl, 2-phenyl-propyl, 2-(4-flurophenyl)-propyl, 2,3-dimethyl-butyl, 2,4,4-timethyl-pentyl and dodecyl; and n has the value of 2 to 50. Preferably n is at least 4.

Particularly favoured aluminoxane products are methylaluminoxane and modified methylaluminoxane. Modified methylaluminoxane is a methylaluminonoxane product which contains a proportion of longer alkyl chain modifiers.

Examples of suitable organoboron compounds are boroxines, $NaBH_4$, triethylborane, tris(pentafluorophenyl)borane, trityl tetrakis(pentafluorophenyl)borate, dimethylanilinium tetrakis(pentafluorophenyl)borate, tributyl borate, dialkylmethylammonium tetrakis(pentafluorophenyl)borate, where alkyl=$C_2$ to $C_{22}$, trialkylammonium tetrakis(pentafluorophenyl)borate, where alkyl=C2 to C22 and the like. These boron containing compounds may be used in conjunction with the $Al(R^1)_3$ compounds discussed above.

The activator may also be or contain a compound that acts as a reducing or oxidising agent, such as sodium or zinc metal and the like, or hydrogen or oxygen and the like.

The activator may be selected from alkylaluminoxanes such as methylaluminoxane (MAO), high stability methylaluminoxane (MAO HS), ethylaluminoxane (EAO), isobutylaluminoxane (iBuAO) as well as modified alkylaluminoxanes such as modified methylaluminoxane (MMAO).

The transition metal source and the aluminoxane may be combined in proportions to provide Al/transition metal molar ratios from about 1:1 to 10 000:1, preferably from about 1:1 to 1000:1, and more preferably from 1:1 to 500:1.

The process in accordance with the second aspect of the invention may include the step of adding to the catalyst system a trialkylaluminium compound in amounts of between 0.01 to 1000 mol per mol of alkylaluminoxane.

In one embodiment of the invention the oligomerisation catalyst includes a combination of
i) a source of Cr; and
ii) a ligating compound of the formula

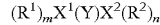

wherein:
$X^1$ and $X^2$ are independently selected from the group consisting of N, P, As, Sb, Bi, O, S and Se; preferably P and N, most preferably P
Y is a linking group between $X^1$ and $X^2$; preferably consisting of —N(R)—, —N(R)—N(R')—, —C(R)(R')—N(R")— or a hydrocarbylene group, where R, R' and R" are H, hydrocarbyl or heterohydrocarbyl groups, preferably hydrocarbyl or heterohydrocarbyl;
m and n are independently 0, 1 or a larger integer, preferably both m and n are 2; and
$R^1$ and $R^2$ are independently hydrogen, a hydrocarbyl group or a heterohydrocarbyl group, and $R^1$ being the same or different when m>1, and $R^2$ being the same or different when n>1.

In this specification the following definitions apply:

A "hydrocarbyl group" as per IUPAC is a univalent group formed by removing one hydrogen atom from a hydrocarbon.

A "hydrocarbylene group" as per IUPAC is a divalent group formed by removing two hydrogen atoms from a hydrocarbon, the free valencies of which are not engaged in a double bond.

A "heterohydrocarbyl group" is a univalent group formed by removing one hydrogen atom from a carbon atom of a heterohydrocarbon, that is a hydrocarbon compound which includes at least one heteroatom (that is not being H or C), and which group covalently bonds with one other moiety through the resultant free valency on that carbon atom.

Most preferably the ligating compound is of the formula

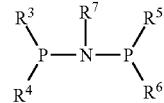

with $R^3$ to $R^7$ as defined above.

Preferably each of $R^3$ to $R^6$ is an alkyl (preferably methyl, ethyl or isopropyl) or aromatic (preferably phenyl or substituted phenyl).

Most preferably each of $R^3$ to $R^6$ is a substituted phenyl

Non limiting examples of the ligating compound are: (phenyl)$_2$PN(methyl)P(phenyl)$_2$; (phenyl)$_2$PN(ethyl)P(phenyl)$_2$; (phenyl)$_2$PN(propyl)P(phenyl)$_2$; (phenyl)$_2$PN(butyl)P(phenyl)$_2$; (phenyl)$_2$PN(pentyl)P(phenyl)$_2$; (phenyl)$_2$PN(hexyl)P(phenyl)$_2$; (phenyl)$_2$PN(heptyl)P(phenyl)$_2$; (phenyl)$_2$PN(octyl)P(phenyl)$_2$; (phenyl)$_2$PN(nonyl)P(phenyl)$_2$; (phenyl)$_2$PN(decyl)P(phenyl)$_2$; (phenyl)$_2$PN(cyclopropyl)P(phenyl)$_2$; (phenyl)$_2$PN(cyclobutyl)P(phenyl)$_2$; (phenyl)$_2$PN(cyclopentyl)P(phenyl)$_2$; (phenyl)$_2$PN(cyclohexyl)P(phenyl)$_2$; (phenyl)$_2$PN(cycloheptyl)P(phenyl)$_2$; (phenyl)$_2$PN(cyclooctyl)P(phenyl)$_2$; (phenyl)$_2$PN(cyclodecyl)P(phenyl)$_2$; (phenyl)$_2$PN(cyclododecyl)P(phenyl)$_2$; (phenyl)$_2$PN(isopropyl)P(phenyl)$_2$; (phenyl)$_2$PN(isobutyl)P(phenyl)$_2$; (phenyl)$_2$PN(secbutyl)P(phenyl)$_2$; (phenyl)$_2$PN(tertiarybutyl)P(phenyl)$_2$; (phenyl)$_2$PN(neopentyl)P(phenyl)$_2$; (phenyl)$_2$PN(1,2-dimethyl-propyl)P(phenyl)$_2$; (phenyl)$_2$PN(allyl)P(phenyl)$_2$; (phenyl)$_2$PN(methylheptyl)P(phenyl)$_2$; (phenyl)$_2$PN(1,5-dimethyl-heptyl)P(phenyl)$_2$; (phenyl)$_2$PN(2-ethylhexyl)P (phenyl)₂; (phenyl)₂PN(adamantyl)P(phenyl)₂; (phenyl)₂PN(adamantylmethyl)P(phenyl)₂; (phenyl)₂PN(3-trimethoxysilane-propyl)P(phenyl)₂; (phenyl)₂PN(indanyl)P(phenyl)₂; (phenyl)₂PN(cyclohexylethyl)P(phenyl)₂; (phenyl)₂PN(2-methylcyclohexyl)P(phenyl)₂; (phenyl)₂PN(cyclohexanemethyl)P(phenyl)₂; (phenyl)₂PN(benzyl)P(phenyl)₂; (phenyl)₂PN(phenyl)P(phenyl)₂; (phenyl)₂PN((4-methoxy)-phenyl)P(phenyl)₂; (phenyl)₂PN((3-methoxy)-phenyl)P(phenyl)₂; (phenyl)₂PN((2-methoxy)phenyl)P(phenyl)₂; (phenyl)₂PN((4-t-butyl)-phenyl)P(phenyl)₂; (phenyl)₂PN((4-nitro)-phenyl)P(phenyl)₂; (phenyl)₂PN(1-naphthyl)P(phenyl)₂; (phenyl)₂PN(2-naphthyl)P(phenyl)₂; (phenyl)₂PN(4-pyridyl)P(phenyl)₂ (phenyl)₂PN(3-(N-morpholine)-propyl)P(phenyl)₂; (phenyl)₂PN(2-naphtyl-ethyl)P(phenyl)₂; (phenyl)₂PN(1-naphtylmethyl)P(phenyl)₂; (phenyl)₂PN(diphenylmethyl)P(phenyl)₂; (phenyl)₂PN(1,2-diphenyl-ethyl)P(phenyl)₂; (phenyl)₂PN(phenylethyl)P(phenyl)₂; (phenyl)₂PN((2-methyl)phenyl)P(phenyl)₂; (phenyl)₂PN((3-methyl)phenyl)P(phenyl)₂; (phenyl)₂PN((4-methyl)phenyl)P(phenyl)₂; (phenyl)₂PN((2,6-dimethyl)phenyl)P(phenyl)₂; (phenyl)₂PN((2-ethyl)-phenyl)P(phenyl)₂; (phenyl)₂PN(1,2,3,4-Tetrahydronaphthyl)P(phenyl)₂; (phenyl)₂PN((2-methyl)cyclohexyl)P(phenyl)₂; (phenyl)₂PN((3-methyl)cyclohexyl)P(phenyl)₂; (phenyl)₂PN((4-methyl)cyclohexyl)P(phenyl)₂; (phenyl)₂PN((2-ethyl)cyclohexyl)P(phenyl)₂; (phenyl)₂PN((2-isopropyl)cyclohexyl)P(phenyl)₂; (phenyl)₂PN((2,6-dimethyl)cyclohexyl)P(phenyl)₂; (phenyl)₂PN(exo-2-norbornanyl)P(phenyl)₂; (phenyl)₂PN(isopinocampheyl)P(phenyl)₂; (phenyl)₂PN(dimethylamino)P(phenyl)₂; (phenyl)₂PN(phthalimido)P(phenyl)₂; (phenyl)₂PN(pyrrolyl)P(phenyl)₂; (phenyl)₂PN(trimethylsiyl)P(phenyl)₂; (phenyl)₂PN(dimethyltertiarybutylsilyl)P(phenyl)₂; [(phenyl)₂P]₂N(1,1'-bis(cyclohexyl)-4,4'-methylene))N[P(phenyl)₂]₂; ([(phenyl)₂P]₂N(1,6-hexylene-)N[P(phenyl)₂]₂; (2,2',2"-triethylamino)[N[P(phenyl)₂]₂]₃; (4-biphenyl)PN(methyl)P(4-biphenyl)₂; (2-naphthyl)₂PN(methyl)P(2-naphthyl)₂; (4-methylphenyl)₂PN(methyl)P(4-methylphenyl)₂; (3-methylphenyl)₂PN(methyl)P(3-methylphenyl)₂; (2-naphthyl)₂PN(methyl)P(phenyl)₂; (2-naphthyl)(phenyl)PN(methyl)P(2-naphthyl)(phenyl); (2-naphthyl)₂PN(methyl)P(2-naphthyl)(phenyl); (2-naphthyl)(phenyl)PN(methyl)P(phenyl)₂; (2-methylphenyl)₂PN(methyl)P(2-methylphenyl)₂; (2-ethylphenyl)₂PN(methyl)P(2-ethylphenyl)₂; (2-isopropylphenyl)₂PN(methyl)P(2-isopropylphenyl)₂; (2-methylphenyl)₂PN(ethyl)P(2-methylphenyl)₂; (2-methylphenyl)₂PN(methyl)P(2-methylphenyl)(phenyl); (2-methylphenyl)(phenyl)PN(isopropyl)P(2-methylphenyl)(phenyl); (2-methylphenyl)₂PN(methyl)P(phenyl)₂; (2-methylphenyl)(phenyl)PN(isopropyl)P(phenyl)₂; (ethyl)₂PN(methyl)P(ethyl)₂; (ethyl)₂PN(isopropyl)P(ethyl)₂; (ethyl)₂PN(tertiarybutyl)P(ethyl)₂; (methyl)₂PN(isopropyl)P(methyl)₂; (isopropyl)₂PN(methyl)P(isopropyl)₂; (ethyl)₂PN(isopropyl)P(ethyl)(phenyl); (ethyl)(phenyl)PN(isopropyl)P(ethyl)(phenyl); (ethyl)₂PN(isopropyl)P(phenyl)₂; (ethyl)(phenyl)PN(isopropyl)P(phenyl)₂; (2-thiopheneyl)₂PN(isopropyl)P(2-thiopheneyl)₂; (diphenylphosphonite)N(isopropyl)(diphenylphosphonite); (dibenzothiaphosphonine)N(isopropyl)(dibenzothiaphosphinine); (dibenzooxaphosphonine)N(isopropyl)(dibenzooxaphosphonine); (phenyl)₂PN(methyl)N(methyl)P(phenyl)₂; (phenyl)₂PN(ethyl)N(ethyl)P(phenyl)₂; (phenyl)₂PN(phenyl)N(phenyl)P(phenyl)₂; (phenyl)₂PN(isopropyl)N(isopropyl)P(phenyl)₂; (phenyl)₂PN(isopropyl)N(methyl)P(phenyl)₂; (phenyl)₂PN(isopropyl)N(methyl)P(phenyl)₂; (4-methylphenyl)₂P—N(CH₃)N(CH₃)—P(4-methylphenyl)₂; (3-methylphenyl)₂P—N(CH₃)N(CH₃)—P(3-methylphenyl)₂; (2-methylphenyl)₂P—N(CH₃)N(CH₃)—P(2-methylphenyl)₂; (2-ethylphenyl)₂P—N(CH₃)N(CH₃)—P(2-ethylphenyl)₂; (2-isopropylphenyl)₂P—N(CH₃)N(CH₃)—P(2-isopropylphenyl)₂; (2-methylphenyl)₂P—N(CH₃)N(CH₃)—P(2-methylphenyl)(phenyl); (2-methylphenyl)₂P—N(CH₃)N(CH₃)—P(phenyl)₂; (ethyl)₂P—N(CH₃)N(CH₃)—P(ethyl)₂; (methyl)₂P—N(CH₃)N(CH₃)—P(methyl)₂; (isopropyl)₂P—N(CH₃)N(CH₃)—P(isopropyl)₂; (ethyl)₂P—N(CH₃)N(CH₃)—P(ethyl)(phenyl); (ethyl)(phenyl)P—N(CH₃)N(CH₃)—P(ethyl)(phenyl); (ethyl)₂P—N(CH₃)N(CH₃)—P(phenyl)₂; (ethyl)(phenyl)P—N(CH₃)N(CH₃)—P(phenyl)₂; (2-thiopheneyl)₂P—N(CH₃)N(CH₃)—P(2-thiopheneyl)₂; (2-naphthyl)₂P—N(CH₃)N(CH₃)—P(2-naphthyl)₂; (4-biphenyl)₂P—N(CH₃)N(CH₃)—P(4-biphenyl)₂; (phenyl)₂P-1,8-naphthyl-P(phenyl)₂; (phenyl)₂P-9,10-phenanthrene-P(phenyl)₂; (phenyl)₂P-4,5-phenanthrene-P(phenyl)₂; (phenyl)₂P—C(CH₃)₂—P(phenyl)₂; (phenyl)₂P—C(CH₂)₂—P(phenyl)₂; (phenyl)₂P-1,2-benzene-P(phenyl)₂; (4-methylphenyl)₂P-1,2-benzene-P(4-methylphenyl)₂; (3-methylphenyl)₂P-1,2-benzene-P(3-methylphenyl)₂; (2-methylphenyl)₂P-1,2-benzene-P(2-methylphenyl)₂; (2-ethylphenyl)₂P-1,2-benzene-P(2-ethylphenyl)₂; (2-isopropylphenyl)₂P-1,2-benzene-P(2-isopropylphenyl)₂; (2-methylphenyl)₂P-1,2-benzene-P(2-methylphenyl)(phenyl); (2-methylphenyl)₂P-1,2-benzene-P(phenyl)₂; (ethyl)₂P-1,2-benzene-P(ethyl)₂; (methyl)₂P-1,2-benzene-P(methyl)₂; (isopropyl)₂P-1,2-benzene-P(isopropyl)₂; (ethyl)₂P-1,2-benzene-P(ethyl)(phenyl); (ethyl)(phenyl)P-1,2-benzene-P(ethyl)(phenyl); (ethyl)₂P-1,2-benzene-P(phenyl)₂; (ethyl)(phenyl)P-1,2-benzene-P(phenyl)₂; (2-thiopheneyl)₂P-1,2-benzene-P(2-thiopheneyl)₂; (2-naphthyl)₂P-1,2-benzene-P(2-naphthyl)₂; (4-biphenyl)₂P-1,2-benzene-P(4-biphenyl)₂; (phenyl)₂P—CH₂CH₂—P(phenyl)₂; (4-methylphenyl)₂P—CH₂CH₂—P(4-methylphenyl)₂; (3-methylphenyl)₂P—CH₂CH₂—P(3-methylphenyl)₂; (4-methylphenyl)₂P—CH₂CH₂—P(4-methylphenyl)(phenyl); (4-methylphenyl)(phenyl)P—CH₂CH₂—P(4-methylphenyl)(phenyl); (4-methylphenyl)₂P—CH₂CH₂—P(phenyl)₂; (4-methylphenyl)(phenyl)P—CH₂CH₂—P(phenyl)₂; (2-methylphenyl)₂P—CH₂CH₂—P(2-methylphenyl)₂; (2-ethylphenyl)₂P—CH₂CH₂—P(2-ethylphenyl)₂; (2-isopropylphenyl)₂P—CH₂CH₂—P(2-isopropylphenyl)₂; (2-methylphenyl)₂P—CH₂CH₂—P(2-methylphenyl)(phenyl); (2-methylphenyl)₂P—CH₂CH₂—P(phenyl)₂; (ethyl)₂P—CH₂CH₂—P(ethyl)₂; (methyl)₂P—CH₂CH₂—P(methyl)₂; (isopropyl)₂P—CH₂CH₂—P(isopropyl)₂; (ethyl)₂P—CH₂CH₂—P(ethyl)(phenyl); (ethyl)(phenyl)P—CH₂CH₂—P(ethyl)(phenyl); (ethyl)₂P—CH₂CH₂—P(phenyl)₂; (ethyl)(phenyl)P—CH₂CH₂—P(phenyl)₂; (2-thiopheneyl)₂P—CH₂CH₂—P(2-thiopheneyl)₂; (phenyl)₂PB(phenyl)P(phenyl)₂; (phenyl)₂PP(phenyl)P(phenyl)₂; (phenyl)₂PSi(methyl)₂P(phenyl)₂; (phenyl)₂AsN(isopropyl)As(phenyl)₂; (phenyl)SN(isopropyl)S(phenyl); (phenyl)₂PN(isopropyl)S(phenyl); (phenyl)₂PN(isopropyl)As(phenyl)₂; (phenyl)₂PN(isopropyl)P(=O)(phenyl)₂; (phenyl)₂P(=O)N(isopropyl)P(=O)(phenyl)₂; (phenyl)₂PN(isopropyl)P(=S)(phenyl)₂; (phenyl)₂P(=S)N(isopropyl)P(=S)(phenyl)₂; (phenyl)₂P(=O)N(isopropyl)P(=S)(phenyl)₂; (4-trifluoromethylphenyl)₂PN(isopropyl)P(4-trifluoromethylphenyl)₂; (4-chlorophenyl)₂PN(isopropyl)P(4-chlorophenyl)₂; (4-methoxyphenyl)₂PN(methyl)P(4-methoxyphenyl)₂; (4-methoxyphenyl)₂PN(isopropyl)P(4-methoxyphenyl)₂; (3-methoxyphenyl)₂PN(methyl)P(3-methoxyphenyl)₂; (4-methoxyphenyl)₂PN(isopropyl)P(4-methoxyphenyl)(phenyl); (4-methoxyphenyl)(phenyl)PN(isopropyl)P(4-methoxyphenyl)(phenyl); (4-methoxyphenyl)₂PN(isopropyl)P(phenyl)₂; (4-methoxyphenyl)(phenyl)PN(isopropyl)P(phenyl)₂; (4-methoxyphenyl)$_2$P—N(CH$_3$)N(CH$_3$)—P(4-methoxyphenyl)$_2$; (3-methoxyphenyl)$_2$P—N(CH$_3$)N(CH$_3$)—P(3-methoxyphenyl)$_2$; (4-methoxyphenyl)$_2$P—N(CH$_3$)N(CH$_3$)—P(4-methoxyphenyl)(phenyl); (4-methoxyphenyl)(phenyl)P—N(CH$_3$)N(CH$_3$)—P(4-methoxyphenyl)(phenyl); (4-methoxyphenyl)$_2$P—N(CH$_3$)N(CH$_3$)—P(phenyl)$_2$; (4-methoxyphenyl)(phenyl)P—N(CH$_3$)N(CH$_3$)—P(phenyl)$_2$; (4-methoxyphenyl)$_2$P-1,2-benzene-P(4-methoxyphenyl)$_2$; (3-methoxyphenyl)$_2$P-1,2-benzene-P(3-methoxyphenyl)$_2$; (4-methoxyphenyl)$_2$P-1,2-benzene-P(4-methoxyphenyl)(phenyl); (4-methoxyphenyl)(phenyl)P-1,2-benzene-P(4-methoxyphenyl)(phenyl); (4-methoxyphenyl)$_2$P-1,2-benzene-P(phenyl)$_2$; (4-methoxyphenyl)(phenyl)P-1,2-benzene-P(phenyl)$_2$; (3-methoxyphenyl)$_2$P(CH$_2$CH$_2$)P(3-methoxyphenyl)$_2$; (3-methoxyphenyl)$_2$P(CH$_2$CH$_2$)P(3-methoxyphenyl)(phenyl); (3-methoxyphenyl)(phenyl)P(CH$_2$CH$_2$CH$_2$)P(3-methoxyphenyl)(phenyl); (3-methoxyphenyl)(phenyl)P(CH$_2$CH$_2$)P(3-methoxyphenyl)(phenyl); (3-methoxyphenyl)(phenyl)P(CH$_2$)P(3-methoxyphenyl)(phenyl); (3-methloxyphenyl)$_2$P(CH$_2$CH$_2$)P(phenyl)$_2$; (3-methoxyphenyl)(phenyl)P(CH$_2$CH$_2$)P(phenyl)$_2$; (4-methoxyphenyl)$_2$P(CH$_2$CH$_2$)P(4-methoxyphenyl)$_2$; (4-methoxyphenyl)$_2$P(CH$_2$CH$_2$)P(4-methoxyphenyl)(phenyl); (4-methoxyphenyl)(phenyl)P(CH$_2$CH$_2$CH$_2$)P(4-methoxyphenyl)(phenyl); (4-methoxyphenyl)(phenyl)P(CH$_2$CH$_2$)P(4-methoxyphenyl)(phenyl); (4-methoxyphenyl)(phenyl)P(CH$_2$)P(4-methoxyphenyl)(phenyl); (4-methoxyphenyl)$_2$P(CH$_2$CH$_2$)P(phenyl)$_2$; (4-methoxyphenyl)(phenyl)P(CH$_2$CH$_2$)P(phenyl)$_2$; (2-methoxyphenyl)$_2$PN(methyl)P(2-methoxyphenyl)$_2$; (2-methoxyphenyl)$_2$PN(ethyl)P(2-methoxyphenyl)$_2$; (2-methoxyphenyl)$_2$PN(phenyl)P(2-methoxyphenyl)$_2$; (2-methoxyphenyl)$_2$PN(methyl)N(methyl)P(2-methoxyphenyl)$_2$; (2-methoxyphenyl)$_2$P(CH$_2$)P(2-methoxyphenyl)$_2$; (2-methoxyphenyl)$_2$P(CH$_2$CH$_2$)P(2-methoxyphenyl)$_2$; tri(2-methoxyphenyl)phosphane; tri(2-methoxymethoxyphenyl)phosphane; (2-methoxyphenyl)$_2$PN(isopropyl)P(2-methoxyphenyl)(phenyl); (2-methoxyphenyl)(phenyl)PN(isopropyl)P(2-methoxyphenyl)(phenyl); (2-methoxyphenyl)$_2$PN(isopropyl)P(phenyl)$_2$; (2-methoxyphenyl)(phenyl)PN(isopropyl)P(phenyl)$_2$; (2-methoxyphenyl)$_2$PN(methyl)P(2-methoxyphenyl)(phenyl); (2-methoxyphenyl)(phenyl)PN(methyl)P(2-methoxyphenyl)(phenyl); (2-methoxyphenyl)$_2$PN(methyl)P(phenyl)$_2$; (2-methoxyphenyl)(phenyl)PN(methyl)P(phenyl)$_2$; (2-ethoxyphenyl)$_2$PN(methyl)P(2-ethoxyphenyl)$_2$; (2-isopropoxyphenyl)$_2$PN(methyl)P(2-isopropoxyphenyl)$_2$; (2-hydroxyphenyl)$_2$PN(methyl)P(2-hydroxyphenyl)$_2$; (2-nitrophenyl)$_2$PN(methyl)P(2-nitrophenyl)$_2$; (2-(dimethylamino)phenyl)$_2$PN(methyl)P(2-(dimethylamino)phenyl)$_2$; (2,3-dimethoxyphenyl)$_2$PN(methyl)P(2,3-dimethoxyphenyl)$_2$; (2,4-dimethoxyphenyl)$_2$PN(methyl)P(2,4-dimethoxyphenyl)$_2$; (2,6-dimethoxyphenyl)$_2$PN(methyl)P(2,6-dimethoxyphenyl)$_2$; (2,4,6-trimethoxyphenyl)$_2$PN(methyl)P(2,4,6-tri-methoxyphenyl)$_2$; (2-methoxyphenyl)(2-methylphenyl)PN(methyl)P(2-methylphenyl)$_2$; (2-methoxymethoxyphenyl)$_2$PN(methyl)P(2-methoxymethoxyphenyl)$_2$; (2-methoxyphenyl)$_2$PN(methyl)P(2-methoxyphenyl)(phenyl); (2-methoxyphenyl)(phenyl)PN(methyl)P(2-methoxyphenyl)(phenyl); (2-methoxyphenyl)$_2$PN(methyl)P(phenyl)$_2$; (2-methoxyphenyl)(phenyl)PN(methyl)P(phenyl)$_2$; (2-methoxyphenyl)$_2$P—N(CH$_3$)N(CH$_3$)—P(2-methoxyphenyl)$_2$; (2-methoxyphenyl)$_2$P-1,2-benzene-P(2-methoxyphenyl)$_2$; (2-methoxyphenyl)$_2$P(CH$_2$CH$_2$)P(2-methoxyphenyl)$_2$; (2-methoxyphenyl)$_2$P(CH$_2$CH$_2$)P(2-methoxyphenyl)(phenyl); (2-methoxyphenyl)(phenyl)P(CH$_2$CH$_2$CH$_2$)P(2-methoxyphenyl)(phenyl); (2-methoxyphenyl)(phenyl)P(CH$_2$CH$_2$)P(2-methoxyphenyl)(phenyl); (2-methoxyphenyl)(phenyl)P(CH$_2$)P(2-methoxyphenyl)(phenyl); (2-methloxyphenyl)$_2$P(CH$_2$CH$_2$)P(phenyl)$_2$; (2-methoxyphenyl)(phenyl)P(CH$_2$CH$_2$)P(phenyl)$_2$; (2-ethoxyphenyl)$_2$P(CH$_2$CH$_2$)P(2-ethoxyphenyl)$_2$; (2-ethoxyphenyl)$_2$P(CH$_2$CH$_2$)P(2-ethoxyphenyl)(phenyl); (2-ethoxyphenyl)(phenyl)P(CH$_2$CH$_2$CH$_2$)P(2-ethoxyphenyl)(phenyl); (2-ethoxyphenyl)(phenyl)P(CH$_2$CH$_2$)P(2-ethoxyphenyl)(phenyl); (2-ethoxyphenyl)(phenyl)P(CH$_2$)P(2-ethoxyphenyl)(phenyl); (2-ethoxyphenyl)$_2$P(CH$_2$CH$_2$)P(phenyl)$_2$; (2-ethoxyphenyl)(phenyl)P(CH$_2$CH$_2$)P(phenyl)$_2$; (2-isopropoxyphenyl)$_2$P(CH$_2$CH$_2$)P(2-isopropoxyphenyl)$_2$; (2-isopropoxyphenyl)$_2$P(CH$_2$CH$_2$)P(2-isopropoxyphenyl)(phenyl); (2-isopropoxyphenyl)(phenyl)P(CH$_2$CH$_2$CH$_2$)P(2-isopropoxyphenyl)(phenyl); (2-isopropoxyphenyl)(phenyl)P(CH$_2$CH$_2$)P(2-isopropoxyphenyl)(phenyl); (2-isopropoxyphenyl)(phenyl)P(CH$_2$)P(2-isopropoxyphenyl)(phenyl); (2-isopropoxyphenyl)$_2$P(CH$_2$CH$_2$)P(phenyl)$_2$; (2-isopropoxyphenyl)(phenyl)P(CH$_2$CH$_2$)P(phenyl)$_2$; (phenyl)$_2$PCH$_2$CH$_2$NHCH$_2$CH$_2$P(phenyl)$_2$; (ethyl)$_2$PCH$_2$CH$_2$NHCH$_2$CH$_2$P(ethyl)$_2$; (phenyl)$_2$PCH$_2$CH$_2$NHCH$_2$CH$_2$P(ethyl)$_2$; (phenyl)(ethyl)PCH$_2$CH$_2$NHCH$_2$CH$_2$P(phenyl)$_2$; (phenyl)SCH$_2$CH$_2$NHCH$_2$CH$_2$S(Phenyl); (ethyl)$_2$PCH$_2$CH$_2$NHCH$_2$CH$_2$P(ethyl)$_2$; (decyl)$_2$PCH$_2$CH$_2$NHCH$_2$CH$_2$P(decyl)$_2$; (phenyl)$_2$PCH$_2$CH$_2$NHCH$_2$CH$_2$S(ethyl); (phenyl)$_2$PCH$_2$CH$_2$P(phenyl)CH$_2$CH$_2$P(phenyl)$_2$ and (phenyl)$_2$PCH$_2$CH$_2$CH$_2$NHCH$_2$CH$_2$P(phenyl)$_2$. (2-fluorophenyl)$_2$PN(isopropyl)P(2-fluorophenyl)$_2$, Ph$_2$PN(Me)P(2-methoxyphenyl)$_2$, (phenyl)$_2$PN(isopropyl)P(phenyl)NH(isopropyl), (phenyl)$_2$PN(isopropyl)P(phenyl)N(phenyl)H, (phenyl)$_2$PN(isopropyl)P(phenyl)N(t-butyl)H, (phenyl)$_2$PN(isopropyl)P(phenyl)N(CH(CH$_3$)(phenyl))H, (phenyl)$_2$PN(CH$_2$)(2-methoxyphenyl)P(phenyl)$_2$, (phenyl)$_2$PN(CH$_2$)$_2$(2-methoxyphenyl)P(phenyl)$_2$, (phenyl)$_2$PN(CH$_2$)$_3$(2-methoxyphenyl)P(phenyl)$_2$,

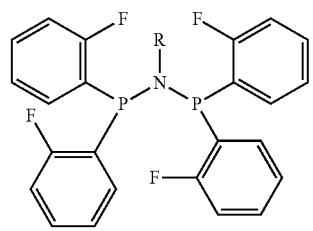

R = iPr

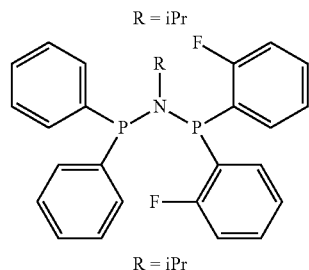

R = iPr

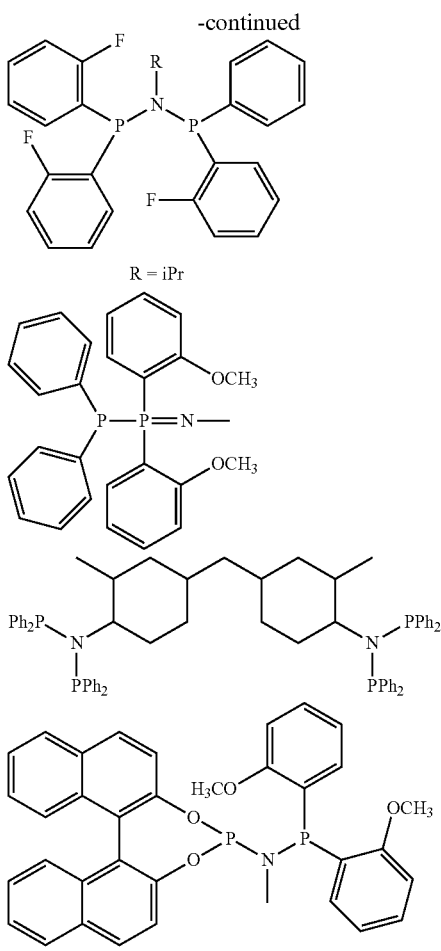

Suitable ligand systems may also include mixtures of the above-mentioned ligands.

The ligating compound may include a polymeric moiety to render the reaction product of the source of transition metal and said ligating compound soluble at higher temperatures and insoluble at lower temperatures e.g. 25° C. This approach may enable the recovery of the complex from the reaction mixture for reuse and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P (phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P (phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

Figure 2:
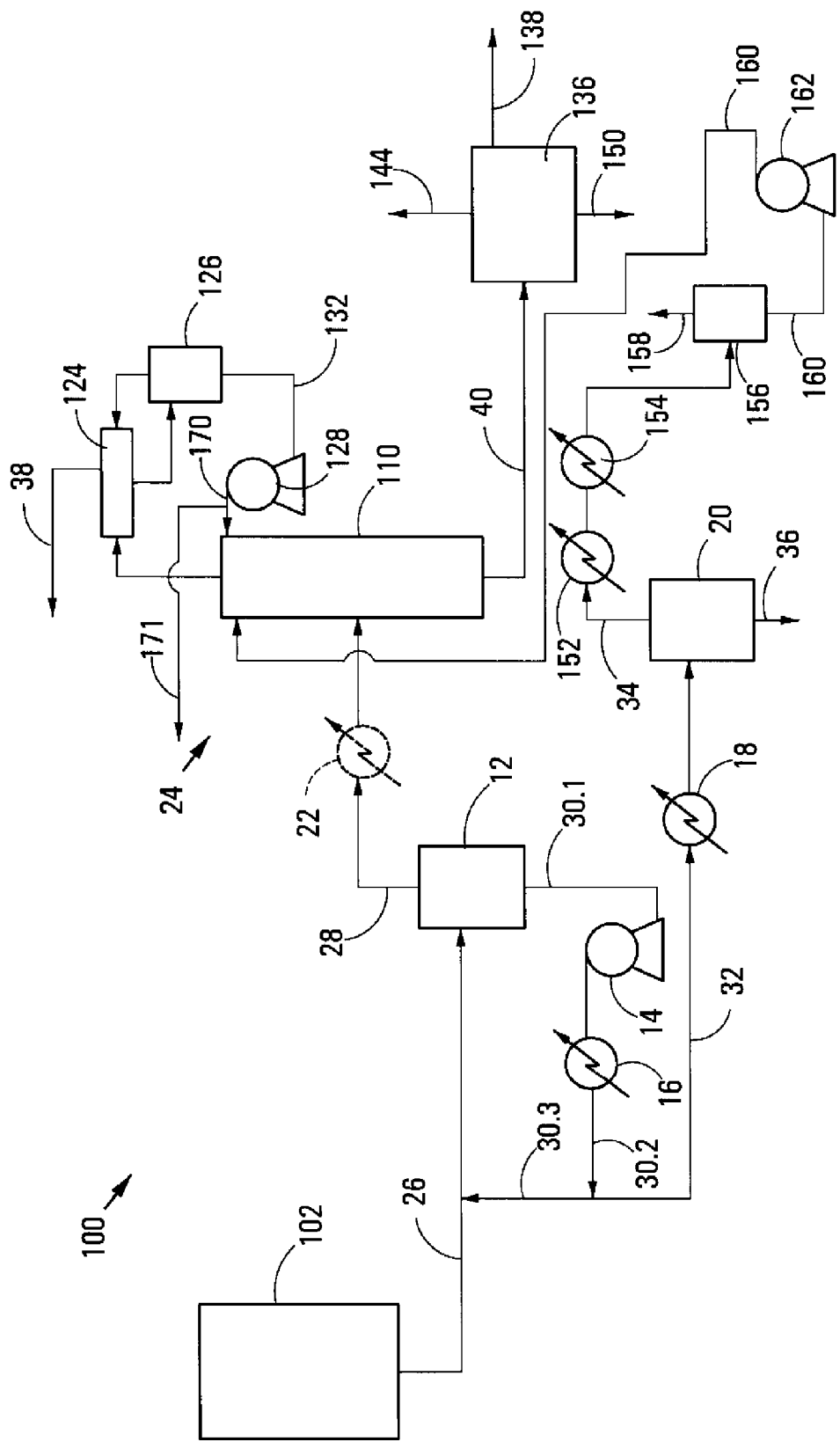
Figure 3:
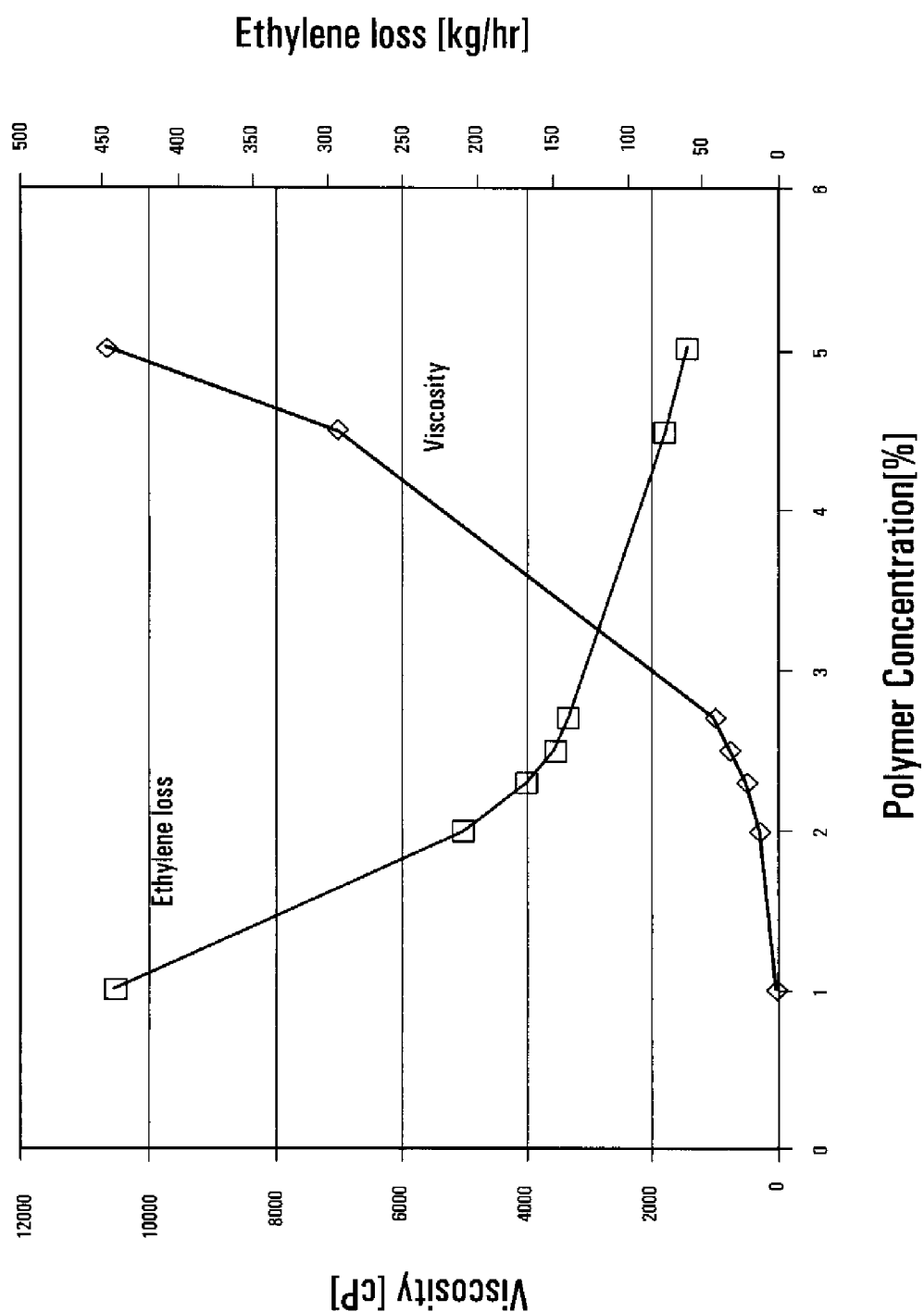

The invention will now be described, by way of non-limiting examples, with reference to the accompanying diagrammatic drawings in which FIG. 1 shows one embodiment of a process in accordance with the invention to separate a multi-component hydrocarbon stream which includes ethylene, at least one polymer and other components;

FIG. 2 shows one embodiment of an ethylene oligomerisation process in accordance with the invention which includes the process of FIG. 1; and FIG. 3 shows graphs of ethylene loss to a first flash stage bottoms product and viscosity of said first flash stage bottoms product as a function of polymer concentration.

Referring to FIG. 1 of the drawings, reference numeral 10 generally indicates one embodiment of a process in accordance with the invention to separate a multi-component hydrocarbon stream which includes ethylene, at least one polymer and other components. Some of the components of the hydrocarbon stream may be present in a plurality of phases. The process 10 is suitable, for example, to separate a product stream from an ethylene oligomerisation reactor, but is not necessarily limited to the separation of a product stream from an ethylene oligomerisation reactor.

The process 10 includes a first flash stage 12 with an associated centrifugal pump 14 and a conventional shell and tube heat exchanger 16. The process 10 also includes a further heat exchanger 18 and a second flash stage 20. In addition, there is a third, optional but preferably present, heat exchanger 22, and an ethylene recovery operation generally indicated by reference numeral 24.

A multi-component hydrocarbon stream line 26 leads to the first flash stage 12. A first ethylene-containing vapour overheads product line 28 leaves a top of the first flash stage 12 to the heat exchanger 22, and runs from the heat exchanger 22 to the ethylene recovery operation 24.

A first flash stage bottoms product line 30.1 leaves a bottom of the first flash stage 12 to the centrifugal pump 14 and runs from the centrifugal pump 14 to the heat exchanger 16. From the heat exchanger 16, a first flash stage bottoms product line 30.2 is taken which then splits into a first flash stage bottoms product line 30.3 and a second flash stage feed line 32. The first flash stage bottoms product line 30.3 joins the multi-component hydrocarbon stream line 26 so that the first flash stage bottoms product lines 30.1, 30.2, 30.3 and the multi-component hydrocarbon stream line 26 form a pump around arrangement.

The second flash stage feed line 32 thus splits off from the first flash stage bottoms product line 30.2 downstream of the heat exchanger 16 and runs to the heat exchanger 18, from where it then runs to enter the second flash stage 20. The second flash stage 20 is provided with a second vapour overheads product line 34 and a second flash stage bottoms product line 36.

The ethylene recovery operation 24 is provided with an ethylene-rich stream line 38 and an ethylene-poor multi-component hydrocarbon stream line 40.

In use, a multi-component hydrocarbon stream which includes ethylene, at least one polymer and other components with possibly some of the components of the hydrocarbon stream being present in a plurality of phases, is fed by means of the multi-component hydrocarbon stream line 26 to the first flash stage 12. Typically, the multi-component hydrocarbon stream includes valuable or desirable hydrocarbon components which are to be separated from other components of the multi-component hydrocarbon stream. For example, the multi-component hydrocarbon stream may include oligomers or olefins, such as 1-hexene and/or 1-octene, which are to be separated from other components of the multi-component hydrocarbon stream. In addition, the multi-component hydrocarbon stream includes ethylene which is valuable and which is to be separated and recovered. The multi-component hydrocarbon stream also includes at least one polymer, which is typically a by-product and which is to be separated from the valuable hydrocarbons and the ethylene. Any polymer present in the multi-component hydrocarbon stream may be present as a solid, or it may be molten or dissolved. Typically however, at the initial temperature of the multi-component hydrocarbon stream, the polymer is a solid and present as a particulate material. One example of such a multi-component hydrocarbon stream is the oligomeric product stream obtained from the oligomerisation, e.g. trimerisation and/or tetramerisation of ethylene, in which case the multi-component hydrocarbon stream typically also includes a diluent solvent, e.g. iso-octane, cyclohexane, methylcyclohexane, propane, isobutane, isopentane, neopentane, 2-methylpentane, or 3-methylpentane, and/or a catalyst solvent, and/or a dissolved catalyst and/or a dissolved catalyst activator.

The multi-component hydrocarbon stream is initially at an elevated pressure of more than 30 bar(a), typically more than 40 bar(a), e.g. 46 bar(a) and an initial temperature of typically between about 40° C. and 80° C., e.g. about 60° C. The multi-component hydrocarbon stream is then heated by direct contact heating or mixing as a result of contact with a hot fluid from the first flash stage bottoms product line 30.3, which is described in more detail hereinafter. Advantageously, any solid polymer in the multi-component hydrocarbon stream can thus be melted and dissolved without the use of a heat exchanger on a hydrocarbon stream which includes polymeric solids. Potential heat exchanger fouling problems are thus avoided. The multi-component hydrocarbon stream is heated to a temperature of at least 150° C., typically about 185° C., as a result of contact and mixing with the hot fluid from the first flash stage bottoms product line 30.3.

In the first flash stage 12, the hot multi-component hydrocarbon stream is flashed from an elevated pressure, e.g. about 46 bar(a) as hereinbefore indicated, and its elevated temperature of say 185° C. to a flash pressure in the range of 10-30 bar(a), e.g. about 15.5 bar(a), with a concomitant drop in temperature. In the first flash stage 12, the multi-component hydrocarbon stream is thus separated by flashing into a first ethylene-containing vapour overheads product which is removed by means of the first ethylene-containing vapour overheads product line 28 and a first flash stage bottoms product which is removed by means of the first flash stage bottoms product line 30.1. Typically, the ethylene-containing vapour overheads product in line 28 includes ethylene in combination with desired product such as oligomeric product, and diluent and/or catalyst solvent. Any light gaseous components of the multi-component hydrocarbon stream, e.g. ethane, will also report to the ethylene-rich stream in line 38. The first flash stage bottoms product also includes some ethylene and desired product and diluent and/or catalyst solvent. Importantly however, the polymer reports to the first flash stage bottoms product in line 30.1.

The first ethylene-containing vapour overheads product is typically at least partially condensed by cooling in the heat exchanger 22 and fed to the ethylene recovery unit operation 24 which typically includes a distillation column. In the ethylene recovery unit operation 24, the first ethylene-containing vapour overheads product is separated into an overhead ethylene-rich stream removed by means of the ethylene-rich stream line 38 and a bottoms ethylene-poor multi-component hydrocarbon stream which is removed by means of the ethylene-poor multi-component hydrocarbon stream line 40.

The heat exchanger 22, if present, may be used for heat integration.

As indicated hereinbefore, the ethylene recovery unit operation 24 typically employs a distillation column. This distillation column typically operates at a pressure of about 10-28 bar(a), preferably about 10-15 bar(a) (the operating pressure of the distillation column is restrained by the flash pressure of the first flash stage 12 and the temperature of a reboiler (not shown) of the ethylene recovery unit operation 24), to generate the ethylene-rich stream and the ethylene-poor multi-component hydrocarbon stream. The main purpose of the ethylene recovery unit operation 24 is to give a predetermined required ethylene recovery. Diluent and/or catalyst solvent may also be recovered with the ethylene. The ethylene-poor multi-component hydrocarbon stream in the stream line 40 thus typically includes the valuable hydrocarbons, e.g. oligomeric product, which it is desired to recover and may also include diluent solvent and/or a catalyst solvent. Conventional separation techniques known to those skilled in the art, such as distillation, may be employed to separate the components of the ethylene-poor multi-component hydrocarbon stream in the stream line 40, if desired.

The flash pressure and the temperature of the multi-component hydrocarbon stream being fed into the first flash stage 12 are selected such that the first flash stage bottoms product in the first flash stage bottoms product line 30.1 has a polymer concentration such that the viscosity of the first flash stage bottoms product in the line 30.1 is less than about 1000 cP at a shear of 1 per second. Typically, when the multi-component hydrocarbon stream is the product stream from an ethylene oligomerisation reaction, this means that the polymer concentration should be less than about 2.8% by mass, as can be seen from FIG. 3 of the drawings. As will be appreciated however, by deliberately operating the first flash stage 12 so that the polymer concentration in the first flash stage bottoms product is limited, thereby to limit the viscosity of the first flash stage bottoms product, ethylene separation from the multi-component hydrocarbon stream is negatively affected leading to an increased loss of ethylene to the first flash stage bottoms product. This is clearly indicated in FIG. 3 of the drawings. In addition, if the multi-component hydrocarbon stream includes any diluent solvent and/or catalyst solvent which is to be recovered, the losses of solvent to the first flash stage bottoms product will also increase.

Although an increased loss of ethylene and solvent, if present, to the first flash stage bottoms product is a negative result of the way in which the first flash stage 12 is operated, the operation of the first flash stage 12 to limit polymer concentration in the first flash stage bottoms product has the advantage that a comparatively cheap conventional centrifugal pump 14 and a conventional shell and tube heat exchanger 16 can be employed to pump the first flash stage bottoms product around and to heat the first flash stage bottoms product.

Hot oil or steam is typically used in the heat exchanger 16 to heat the first flash stage bottoms product, for example to a temperature in the range of about 190° C. to 300° C. The discharge pressure of the pump 14 is typically such that substantially no vapourisation occurs downstream of the heat exchanger 16. A large portion of the heated first flash stage bottoms product is returned to the multi-component hydrocarbon stream line 26 by means of the flow lines 30.2 and 30.3 thereby to heat the multi-component hydrocarbon stream to a temperature of more than 150° C. Typically, about 90% of the heated first flash stage bottoms product is pumped around and thus returned to the multi-component hydrocarbon stream line 26. The first flash stage 12 must thus be designed to accommodate the high recycle rate and hence the high throughput.

The balance of the heated first flash stage bottoms product is fed by means of the second flash stage feed line 32 to the heat exchanger 18, where it is heated to a temperature above 190° C., and thereafter fed into the second flash stage 20. In the second flash stage 20, the second flash stage feed from the line 32 is flashed to a pressure of less than 10 bar(a), e.g. about 4 bar(a) and thus separated into a second vapour overheads product removed by means of the second vapour overheads product line 34 and a second flash stage bottoms product removed by means of the second flash stage bottoms product line 36. As will be appreciated, the second vapour overheads product includes a significant amount of ethylene and possibly diluent solvent and/or catalyst solvent as a result of the operating conditions selected for the first flash stage 12, which it may be desirable to recover.

The second flash stage bottoms product is typically fed to a devolatiliser (not shown) by means of the second flash stage bottoms product line 36. The temperature and pressure of the flash operation in the second flash stage 18 are thus typically selected such that the second flash stage bottoms product can be fed to a devolatiliser. The devolatiliser produces a solids stream which may for example be subjected to an underwater pelletiser to pelletise the solids, which is mostly made up of polymeric material.

Referring to FIG. 2 of the drawings, one embodiment of an ethylene oligomerisation process in accordance with the invention, which includes the separation process 10, is shown and generally indicated by reference numeral 100.

The process 100 includes an oligomerisation reactor 102 producing a mostly liquid bottoms product which is removed by the multi-component hydrocarbon stream line 26.

In FIG. 2, more detail of the ethylene recovery unit operation 24 is also shown. Thus, in the process 100, the ethylene recovery unit operation 24 includes an ethylene recovery distillation column 110 provided with a partial condenser 124, a reflux drum 126 and a pump 128. The ethylene-rich stream line 38, which is in fact an ethylene vapour recycle line to the reactor 102, thus leaves the partial condenser 124 and is returned to the reactor 102. A reflux line 132 leaves the reflux drum 126 and passes to the pump 128. An increased pressure reflux line 170 leads from the pump 128 to the ethylene recovery distillation column. The increased pressure reflux line 170 may branch off into a flow line 171 which returns to the reactor 102. Alternatively, the flow line 171 may branch off the reflux line 132.

The ethylene-poor multi-component hydrocarbon stream line 40 leaves the ethylene recovery distillation column 110 and feeds into a product work-up section generally indicated by reference numeral 136. The product work-up section 136 typically operates at a lower pressure than the ethylene recovery distillation column 110 and uses distillation (fractionation) to separate the ethylene-poor multi-component hydrocarbon stream into different products, e.g. 1-hexene, 1-octene, a C10+ product, and the like. One or more olefinic product lines, represented by the line 138, thus lead from the product work-up section 136. The product work-up section 136 is also provided with a vapour purge line 144. In addition, the product work-up section 136 may be provided with a diluent solvent recycle line 150 which is ultimately returned to the reactor 102.

In the process 100, two condensers 152 and 154 are provided in the second vapour overheads product line 34, with the second vapour overheads product line 34 running into a vapour/liquid separator 156 downstream of the condenser 154. The separator 156 is provided with a vapour line 158 and a condensate line 160. The condensate line 160 runs via a pump 162 to the ethylene recovery distillation column 110. It is to be appreciated that the condensers 152 and 154 can be replaced by a single condenser partially or completely condensing ethylene in the second vapour overheads product from the second flash stage 20.

The process 100 is used to oligomerise a hydrocarbon, i.e. ethylene, to form at least one alpha-monomer or co-monomer product. The process 100 as shown in FIG. 2 is in particular suitable for the tetramerisation of ethylene to produce 1-octene and 1-hexene as desirable products.

In use, in one non-limiting example or embodiment of the process of the invention employing a bubbling column reactor, the reactor 102 contains a bulk liquid phase in the form of a bubbling column. The reactor 102 in this non-limiting example or embodiment is thus a bubbling column reactor. Recycled ethylene (from the ethylene-rich stream line 38 and the flow line 171) as hydrocarbon reactant, together with fresh ethylene feed (not shown) and recycled diluent solvent are typically condensed and fed into the bottom of the reactor 102. Although not shown, the recycled ethylene (from the ethylene-rich stream line 38 and from the flow line 171) would first undergo an operation to increase the pressure to that of the reactor 102. Said pressure-increasing operation could include a compressor and/or a pump. The reactor 102 is operated typically at a pressure of between about 45 bar(a) and 50 bar(a), with the bulk liquid phase being at a temperature below its boiling point at the operating pressure of the reactor 102. Typically, this temperature is about 60° C. The bulk liquid phase of the reactor 102 includes an admixture of ethylene, oligomeric products (alpha-monomer or co-monomer polymeric or oligomeric products, in this case 1-octene and 1-hexene), a solvent which includes a dissolved catalyst system, a reaction or diluent solvent, and small amounts of polymeric solids formed by undesirable side reactions. A reaction solvent or diluent solvent, i.e. an inert liquid component which does not take part in a polymerisation or oligomerisation reaction and which is not required to ensure that the polymerisation or oligomerisation reaction takes place, is used for the polymerising or oligomerising, e.g. tetramerisation, of a hydrocarbon such as ethylene, to reduce secondary incorporation of alpha monomer or co-monomer products, e.g. 1-hexene or 1-octene, into undesirable longer chain products of less value, by diluting the concentration of the primary reaction product or products. The diluent solvent may be lower boiling or higher boiling than the lowest-boiling desirable oligomeric product (e.g. 1-hexene) from the reactor 102. The operation of a boiling bubble column reactor for the oligomerisation of ethylene and which employs a diluent solvent is known to those skilled in the art and as an understanding of the operation of the reactor 102 is not required for an understanding of the present invention, the operation of the reactor 102 is not discussed in any detail. It suffices to appreciate that the reactor 102 produces a liquid effluent stream which is the multi-component hydrocarbon stream in the multi-component hydrocarbon stream line 26 hereinbefore described.

In the process 100, the multi-component hydrocarbon stream is thus flashed in the first flash stage 12 as hereinbefore described, with the first ethylene-containing vapour overheads product being fed into the ethylene recovery distillation column 110 after having been partially condensed and with the second flash stage feed being fed to the second flash stage 20 to produce the second vapour overheads product in the second vapour overheads product line 34 and the second flash stage bottoms product in the second flash stage bottoms product line 36.

The second vapour overheads product from the second flash stage 20 is fed by means of the second vapour overheads product line 34 to the condensers 152, 154. Surprisingly, simulations show that the temperature and pressure combinations required for the condensers 152, 154 to substantially completely condense all of the ethylene present in the second vapour overheads product (and all diluent solvent, if any diluent solvent is present), are reasonable and comparatively insensitive to both the diluent solvent used in the reactor 102 as well as the degree of dilution or the viscosity of the first flash stage bottoms product in the first flash stage bottoms product line 30.1. Results for two cases, in which the viscosity of the first flash stage bottoms product were respectively above and below 1000 cP shear 1 per second (i.e. in which the polymer concentrations were respectively comparatively high and comparatively low) are shown in Table 1.

TABLE 1

Simulation results for required pressure of second flash stage 20 for complete condensation of ethylene and diluent solvent in the second vapour overheads product for various diluent solvents and for various cooling utility temperatures

| Diluent solvent | Condenser cooling utility temperature [° C.] | Second flash stage 20 flash pressure [bar(a)] Low Viscosity Case (<1000 cP) | Second flash stage 20 flash pressure [bar(a)] High Viscosity Case (>1000 cP) |
|---|---|---|---|
| Isobutane | −2 | 2.2 | 2.1 |
|  | 0 | 2.3 | 2.1 |
|  | 5 | 2.5 | 2.3 |
| Isopentane | −2 | 2.2 | 2.1 |
|  | 0 | 2.3 | 2.1 |
|  | 5 | 2.5 | 2.3 |
| Iso-octane | −2 | 2.2 | 2.1 |
|  | 0 | 2.3 | 2.1 |
|  | 5 | 2.5 | 2.3 |

It can be seen that, for both cases, even at pressures as low as 2.1 to 2.5 bar(a), the second vapour overheads product could be condensed at temperatures as high as 5° C.

Simulations show that the second vapour overheads product temperature would typically be well in excess of 200° C. In cooling this stream down to be condensed, heat integration may be achieved. The second vapour overheads product in the second vapour overheads product line 34 may therefore be used as a utility to heat another process stream elsewhere in the process 100 or for generating low pressure steam from steam condensate. This has the advantage of eliminating the requirements for air-cooling of the second vapour overheads product. After heat integration to cool the second vapour overheads product, the second vapour overheads product may be cooled further using either plant cooling water, chilled water or refrigerant to achieve the required degree of condensation of the second vapour overheads product.

As refrigerant is an expensive cooling utility, additional simulations were performed to quantify the recovery of ethylene to the condensate line 160 from the vapour/liquid separator 156, that is achievable with plant cooling water alone (i.e. partial condensation). The results are shown in Table 2 for various diluent solvents and flash pressures for the second flash stage 20. These simulation projections show that a considerable amount of ethylene can be recovered at reasonable operating pressures for the second flash stage 20 using plant cooling water alone.

TABLE 2

Percentages of ethylene recoverable to liquid phase using plant cooling water at different second flash stage 20 flash pressures, for various diluent solvents

| Pressure [bar(a)] | Iso-octane (% ethylene recovered) | Isopentane (% ethylene recovered) | Neopentane (% ethylene recovered) | Isobutane (% ethylene recovered) | Propane (% ethylene recovered) |
|---|---|---|---|---|---|
| 4 | 84 | 80 | 67 | 37 | 10 |
| 5 | 100 | 100 | 98 | 68 | 15 |
| 6 | 100 | 100 | 100 | 98 | 23 |
| 7 | 100 | 100 | 100 | 100 | 31 |
| 8 | 100 | 100 | 100 | 100 | 47 |
| 9 | 100 | 100 | 100 | 100 | 68 |
| 10 | 100 | 100 | 100 | 100 | 94 |

The condensate in the condensate line 160 from the vapour/liquid separator 156 thus contains ethylene and, potentially, diluent solvent. In the process 100, the condensate is pumped up to the operating pressure of the ethylene recovery distillation column 110 using the pump 162 and pumped to the ethylene recovery distillation column 110. As such, all ethylene and, in the case of a diluent solvent boiling lower than the oligomeric product, e.g. boiling lower than 1-hexene, also all of the diluent solvent, may be recovered in the ethylene recovery distillation column 110, and recycled to the reactor 102 via the partial condenser 124 and the ethylene-rich stream line 38 and the flow line 171.

It is to be noted that the condensate in the condensate line 160 may be introduced into the ethylene recovery distillation column 110 either as a separate feed point as shown in FIG. 2, or combined with the first ethylene-containing vapour overheads product in the first ethylene-containing vapour overheads product line 28 downstream of the heat exchanger (partial condenser) 22. Simulations show that, once pumped up to the ethylene recovery distillation column 110 operating pressure, the condensate in the condensate line 160 should not be heated to temperatures above that of the first ethylene-containing vapour overheads product as this places additional load on the partial condenser 124. Simulations further show that the condensate in the condensate line 160 can be introduced into the partial condenser 124, reflux drum 126 or reflux line 132 without compromising the specification on the ethylene-rich steam in the ethylene-rich stream line 38.

Any vapour separated in the vapour/liquid separator 156 is purged via the vapour line 158. Instead of purging at this point, e.g. by flaring, the vapour line 158 may be routed to join the ethylene-poor multi-component hydrocarbon stream line 40 so that the vapour is routed to the product work-up section 136.

As mentioned above, the condensate in the condensate line 160 may also be joined with the first ethylene-containing vapour overheads product in the first ethylene-containing vapour overheads line 28. This does however require the mixing of a liquid and partially condensed vapour stream. Simulations further show that, from a thermodynamic point of view it is most advantageous to introduce the condensate line 160 at a separate feed point on the ethylene recovery distillation column 110. The most desirable point of introduction of the condensate in the condensate line 160 into the ethylene recovery distillation column 110 depends on the diluent solvent used in the reactor 102.

A number of cases have been simulated with the following diluent solvents for the reactor 102: propane, isobutene, isopentane, iso-octane and methylcyclohexane. In the case of the reactor 102 producing 1-hexene as the lowest boiling desired product and using a diluent solvent that has a boiling point lower than that of 1-hexene, the process of FIG. 2 is particularly advantageous, as such a low-boiling diluent solvent may be recovered and recycled with the ethylene in the ethylene recovery distillation column 110. In such a case, it is thus desirable to route all of the low-boiling diluent solvent to the ethylene recovery distillation column 110. When the first flash stage 12 is however operated to limit polymer concentration to below 5%, a significant fraction of diluent solvent, whether lower or higher boiling than 1-hexene, reports to the first flash stage bottoms product in the first flash stage bottoms product line 30.1. Ultimately, the diluent solvent thus reports to the condensate in the condensate line 160. In the case of a diluent solvent higher boiling than 1-hexene, this is not a problem as the diluent solvent can be recovered in the product work-up section 136, by simply feeding the second vapour overheads product to the product work-up section 136. In the case of a low-boiling diluent solvent, the opportunity for eliminating additional distillation steps to recover this diluent solvent by recovering it with the ethylene in the ethylene recovery distillation column 110 would however be lost if the second vapour overheads product is routed to the product work-up section 136. It is thus an advantage to condense the second vapour overheads product in the second vapour overheads product line 34 thereby to recover the low-boiling diluent solvent by means of the ethylene recovery distillation column 110.

In some embodiments of the process 100, which are not illustrated, ethylene in the vapour line 158 from the vapour/liquid separator 156 is recovered by means of absorption into a liquids process stream. In these embodiments of the process of the invention, in which the condensers 152, 154 only partially condense the ethylene in the second vapour overheads product, the vapour in the vapour line 158 is combined with an appropriate liquid process stream from elsewhere in the process 100 such that the vapour stream is partially or completely absorbed into the liquid process stream. This liquid process stream, now containing the uncondensed, otherwise lost, ethylene may now be routed to a part of the process 100 where the ethylene can be used. Examples of these embodiments are as follows:

EXAMPLE 1

The vapour in the vapour line 158 is absorbed in the diluent solvent recycle line 150 from the product work-up section 136. This example is applicable to the case where the process 100 produces 1-hexene and 1-octene as desirable products and the diluent solvent used in the reactor 102 boils at a temperature between 1-hexene and 1-octene (e.g. iso-octane). The diluent solvent is thus recovered in the product work-up section 136 using conventional distillation. The diluent solvent recycle in the diluent solvent recycle line 150 is at a lower pressure than the vapour in the vapour line 158 and a combination of these two streams is therefore particularly favourable. If the diluent solvent recycle in the diluent solvent recycle line 150 undergoes additional purification before being recycled to the reactor 102, the vapour in the vapour line 158 may be combined with the diluent solvent in the diluent solvent recycle line 150 either before or after this additional purification step. Alternatively, the vapour in the vapour line 158 may be combined with a slipstream of the diluent solvent recycle line 150 such that a diluent recycle stream free of ethylene is also available to the process 100.

EXAMPLE 2

In this example, the vapour in the vapour line 158 is absorbed into a slipstream of any one of the product streams represented by the product stream line 138. These product streams (e.g. a 1-hexene product stream and a 1-octene product stream and a C10+ hydrocarbon product stream) are also available at a lower pressure than the pressure of the vapour in the vapour line 158, facilitating combination with a slipstream of one or more of these product streams. In this example, the combined stream obtained by combining the vapour in the vapour line 158 with a product slipstream is routed back to the ethylene distillation recovery column 110 for recovery of the ethylene.

EXAMPLE 3

The vapour in the vapour line 158 in this example is absorbed into any process stream that is used for defouling of equipment, whereafter the stream is reprocessed by means of the first flash stage 12 and the second flash stage 20 and the ethylene recovery distillation column 110. For example, should either a 1-octene or a C10+ hydrocarbon stream be used for defouling the reactor 102, the vapour in the vapour line 158 may be combined with any of these streams either before the defouling step or in wash effluent from the reactor 102 after defouling.

The process 10,100 of the invention, as illustrated, has the advantage that it significantly reduces the solution viscosity of the first flash stage bottoms product and hence allows the use of lower cost equipment to pump and heat the first flash stage bottoms product. In the process 10,100 as illustrated, it is also possible to use a lower temperature, or a higher pressure, in the first flash stage 12 as less product is taken overheads. In the process 100, as illustrated, full recovery of ethylene from the first flash stage 12 and the second flash stage 20 is possible, and the process 100 as illustrated also allows for full recovery of diluent solvents lower boiling than 1-hexene via the ethylene recovery distillation column 110 thereby eliminating the need for further diluent solvent recovery separation steps downstream of the ethylene recovery distillation column 110.

The invention claimed is:

1. A process to separate a multi-component hydrocarbon stream which includes ethylene, at least one polymer and other components, the process comprising:
in a first flash stage, flashing the multi-component hydrocarbon stream, from an elevated pressure of more than 30 bar(a) and an elevated temperature in the range of 150° C. to 185° C. to a flash pressure in the range of 10 bar(a) to 30 bar(a), producing a first ethylene-containing vapour overheads product at a pressure in the range of 10 bar(a) to 30 bar(a) and a first flash stage bottoms product which includes some ethylene, said at least one polymer and some of said other components, the flash pressure and the elevated temperature of the multi-component hydrocarbon stream being selected such that the first flash stage bottoms product has a concentration of said at least one polymer of less than 5% by mass to render the viscosity of the first flash stage bottoms product at the temperature of the first flash stage bottoms product in the first flash stage at less than 1000 cP at a shear of 1 per second;
heating at least a portion of the first flash stage bottoms product to a temperature in excess of 150° C. to form a heated first flash stage bottoms product;
combining a recycle portion of said heated first flash stage bottoms product with the multi-component hydrocarbon stream, which is at a temperature less than 150° C. before combination with said recycle portion, thereby to heat the multi-component hydrocarbon stream to said elevated temperature in the range of 150° C. to 185° C.;

withdrawing at least a portion of the first flash stage bottoms product which includes some ethylene, said at least one polymer and some of said other components, from the first flash stage; and removing the first ethylene-containing vapour overheads product from the first flash stage.

2. The process as claimed in claim 1, further comprising:

feeding said withdrawn portion of the first flash stage bottoms product which includes some ethylene, said at least one polymer and some of said other components to a second flash stage as a second flash stage feed; and flashing the second flash stage feed in the second flash stage to produce a second vapour overheads product which includes most of the ethylene in the second flash stage feed, and a second flash stage bottoms product which includes most of said at least one polymer in the second flash stage feed.

3. The process as claimed in claim 1, further comprising:

subjecting said first ethylene-containing vapour overheads product removed from the first flash stage to at least one ethylene recovery unit operation producing an ethylene-rich stream and an ethylene-poor multi-component hydrocarbon stream.

4. The process as claimed in claim 2, further comprising:

subjecting said first ethylene-containing vapour overheads product removed from the first flash stage to at least one ethylene recovery unit operation producing an ethylene-rich stream and an ethylene-poor multi-component hydrocarbon stream;

condensing or partially condensing the second vapour overheads product from the second flash stage to produce a condensate; and feeding the condensate to the ethylene recovery unit operation.

5. The process as claimed in claim 1, in which the concentration of polymers in the first flash stage bottoms product is less than 3% by mass.

6. The process as claimed in claim 2, in which said portion of the first flash stage bottoms product fed to the second flash stage as the second flash stage feed is split off from the heated first flash stage bottoms product, the process including further heating the second flash stage feed before flashing the second flash stage feed in the second flash stage.

7. An ethylene oligomerisation process, the process comprising:

in an oligomerisation stage, oligomerising ethylene and withdrawing a multi-component hydrocarbon stream which includes unreacted ethylene, at least one polymer and other components;

separating the multi-component hydrocarbon stream in accordance with a process as claimed in claim 2, producing said first ethylene-containing vapour overheads product and said second vapour overheads product;

feeding the first ethylene-containing vapour overheads product to an ethylene recovery unit operation producing an ethylene-rich stream and an ethylene-poor multi-component hydrocarbon stream which includes oligomeric product;

recycling the ethylene rich stream to the oligomerisation stage;

recovering ethylene from the second vapour overheads product; and recycling said ethylene recovered from the second vapour overheads product to the oligomerisation stage.

8. The process as claimed in claim 7, further comprising:

at least partially condensing the second vapour overheads product from the second flash stage to provide a second flash stage condensate product; and pumping the second flash stage condensate product to said ethylene recovery unit operation, recovering ethylene from the second vapour overheads product thus being effected in said ethylene recovery unit operation.

9. The process as claimed in claim 8, in which plant cooling water is used as cooling medium partially to condense the second vapour overheads product at a pressure ranging between 4 bar(a) and 10 bar(a).

10. The process as claimed in claim 7, in which the ethylene is oligomerised in the presence of a diluent solvent, the diluent solvent being selected from the group consisting of iso-octane, iso-pentane, neopentane, isobutane and mixtures of two or more of these.

11. The process as claimed in claim 7, in which the second flash stage feed is flashed in the second flash stage to a pressure of between 1 bar(a) and 6 bar(a).

12. The process as claimed in claim 7, in which the ethylene recovery unit operation employs at least one distillation column, said distillation column being operated at the same pressure as the first flash stage, minus any pressure drop caused by intervening process equipment, so that said distillation column thus operates at a pressure in the range of 10 bar(a) to 28 bar(a), with the first ethylene-containing vapour overheads product being fed to the ethylene recovery unit operation being at least partially condensed before being fed into the ethylene recovery unit operation.

13. The process as claimed in claim 7, in which, in the oligomerisation stage, the ethylene is oligomerised at an elevated pressure of at least 30 bar(a) and at an elevated temperature of at least 40° C., with the ethylene-poor multi-component hydrocarbon stream from the ethylene recovery unit operation including alpha monomers or co-monomers.

14. The process as claimed in claim 7, which is predominantly a trimerisation of ethylene process employing a trimerisation catalyst system, or which is predominantly a tetramerisation of ethylene process employing a tetramerisation catalyst system.

* * * * *